US007060432B1

(12) United States Patent
Hyldig-Nielsen et al.

(10) Patent No.: US 7,060,432 B1
(45) Date of Patent: Jun. 13, 2006

(54) METHODS FOR THE DETECTION, IDENTIFICATION, AND/OR ENUMERATION OF YEAST, PARTICULARLY IN WINE

(75) Inventors: Jens J. Hyldig-Nielsen, Moss Beach, CA (US); Heather P. O'Keefe, Lexington, MA (US); Henrik Stender, Gentofte (DK)

(73) Assignee: Applera Corporation, Framingham, MA (US)

( * ) Notice: Subject to any disclaimer, the term of this patent is extended or adjusted under 35 U.S.C. 154(b) by 692 days.

(21) Appl. No.: 09/593,914

(22) Filed: Jun. 14, 2000

Related U.S. Application Data

(60) Provisional application No. 60/139,212, filed on Jun. 15, 1999.

(51) Int. Cl.
*C12Q 1/68* (2006.01)
*C07H 21/02* (2006.01)
*C07H 21/04* (2006.01)

(52) U.S. Cl. ............... 435/6; 435/40.5; 435/40.51; 536/23.1; 536/23.74; 536/24.3; 536/24.32

(58) Field of Classification Search .................. 435/6, 435/91.2, 870, 91.1; 536/23.1, 23.74, 24.3, 536/24.32, 24.33
See application file for complete search history.

(56) References Cited

U.S. PATENT DOCUMENTS

| 4,299,853 A | 11/1981 | Kleyn ................. 426/271 |
| 4,666,719 A | 5/1987 | Spiller ................. 426/18 |
| 5,151,354 A | 9/1992 | Strasser et al. .......... 435/161 |
| 5,376,528 A | 12/1994 | King et al. ................ 435/6 |
| 5,484,909 A | 1/1996 | Nietupski et al. ....... 536/24.32 |
| 5,539,082 A | 7/1996 | Nielsen et al. ............ 530/300 |
| 5,645,830 A | 7/1997 | Reid et al. ............ 424/93.45 |
| 5,677,166 A | 10/1997 | Broadbent et al. ....... 435/252.3 |
| 5,705,339 A | 1/1998 | Nietupski et al. ............. 435/6 |
| 5,888,733 A | 3/1999 | Hyldig-Nielsen et al. ....... 435/6 |
| 5,905,038 A * | 5/1999 | Parton ................. 435/287.6 |
| 5,985,563 A | 11/1999 | Hyldig-Nielsen et al. ....... 435/6 |

FOREIGN PATENT DOCUMENTS

| EP | 0422872 A | 4/1991 |
| EP | 0497464 A | 8/1992 |
| EP | 0890650 A2 | 1/1999 |
| WO | WO97/14026 | 4/1997 |
| WO | WO98/15648 | 4/1998 |
| WO | WO98/24933 | 6/1998 |
| WO | 99/10533 * | 3/1999 |
| WO | WO99/41273 | 8/1999 |

OTHER PUBLICATIONS

De Wachter et al. GenBank Accession No. X58052. Dec. 1992.*

Amann et al. Microbiological Reviews. Mar. 1995. 59(1): 143-169.*

Boston Probes, Inc. PNA Micro ID FISH Reagent Kit User Guide. May 16, 2000.

Cai, J. et al., Phylogenetic relationships among members of the Ascomycetous yeast genera. *Brettanomyces, Debaryomyces, Dekkera,* and *Kluyveromyces* deduced by small-subunit rRNA gene sequences. Intl. J. Systematic Bacteriology 46, 542-549 (1996).

Dudley, E.C. editor, The Unity of Evolutionary Biology: Proceedings of the Fourth International Congress of Systematic and Evolutionary Biology. vol. II (1990).

Fleurent, J. et al, Rapid genetic Identification of Indigenous yeast species found In grape must or wine. Am. J. Enol. 48, 385 (1997).

Heidelberg, J.F. et al, Enumeration of *vibrio vulnificus* on membrane filters with a fluorescently labeled oligonucleotide probe specific for kingdom-level 16S rRNA sequences. Appl. & Environ. Microbio. 59, 3474 (1993).

Hoeben, P. et al, Larger rearranged mitochondrial gnomes In *Dekkera/Brettanomyces* yeasts are more closely related than smaller genomes with a conserved gene order. J. Mol. Evol. 36, 263-269 (1993).

Ibeas, J.I. et al, Detection of *Dekkera-Brettanomyces* strains In sherry by a nested PCR method. Appl. Environ. Microbio. 62, 998-1003 (1996).

Liu, C.-H. et al, The Isolation and Identification of microbes from a fermented tea beverage, Haipao, and their Interactions during Haipao fermentation. Food Microbio. 13, 407-415 (1996).

(Continued)

*Primary Examiner*—Carla J. Myers
(74) *Attorney, Agent, or Firm*—Brian D. Gildea

(57) ABSTRACT

This invention is related to novel probes, probe sets, methods and kits pertaining to the detection, identification and/or quantitation of yeasts and particularly *Dekkera bruxellensis* (a.k.a. *Brettanomyces*) an organism that spoils wine. Preferred probes for the detection of one or more species of the *Dekkera/Brettanomyces* genus comprise a probing nucleobase sequence, at least a portion of which is selected from the group consisting of: AGC-GGG-TCT-ATT-AGA (Seq. ID No. 1); CCA-GGT-GAG-GGT-CGC (Seq. ID No. 2); CGG-TTG-CCC-GAT-TTC (Seq. ID No. 3); TCG-CCT-TCC-TCC-TCT (Seq. ID No. 4); CGG-TCT-CCA-GCG-ATT (Seq. ID No. 5); CAC-AAG-ATG-TCC-GCG (Seq. ID No. 6); GCG-GGC-ACT-AAT-TGA (Seq. ID No. 7); CAT-CCA-CGA-GGA-ACG (Seq. ID No. 8); GTG-TAA-ACC-AGG-TGC (Seq. ID No. 9); ATG-GCT-CCC-AGA-ACC (Seq. ID No. 10) and GAC-AGA-ATC-GAA-GGG (Seq. ID No. 11). The probes, probe sets, methods and kits of this invention are particularly well suited for use in the analysis of yeast in wine, beer and liquor and in the monitoring of contamination of in-process product as well as the equipment and facilities used to manufacture product in wineries and breweries.

20 Claims, 3 Drawing Sheets

OTHER PUBLICATIONS

Millipore Corporation, *Brettanomyces* Assay Data Sheet, believed to be first published after Jun. 15, 1999.

Millipore Corporation, *Brettanomyces* ID Assay Starter Kit, Product Literature, believed to be first published after Jun. 15, 1999.

Mitrakuk, C. et al, Identification of *Brettanomyces/Dekkera* yeasts from Californian wines. Am. J. Enol. Vitic. 48, 390 Abstract (1997).

Pluskal, M. et al, Peptide nucleic acid probes and their application In DNA and RNA blot hybridization analysis. American Soc. for Biochem. and Mol. Bio. 85th Annual Meeting (1994) Abstract #35.

Smith, M. Th. et al, *Dekkera, Brettanomyces* and *Eeniella*: Electrophoretic comparison of enzymes and DNA-DNA homology. Yeast 6, 299-310 (1990).

Soler, A.A. et al, PCR-amplification of the histidine decarboxylase coding region from histamine producing yeasts. 95th ASM General Meeting, Abstract #H-27.

Stender, H. et al, A probe-based method for rapid Identification and enumeration of *Brettanomyces* In wine. 50th Annual Meeting American Society for Enology and Viticulture abstract, Jun. 30, 1999.

Yamada, Y. et al, The phylogenetic relationships of *Eeniella nana* Smith, Batenburg-van der Vegte et Scheffers based on the partial sequences of 18S and 26S ribosomal RNAs (Candidaceae). J Industrial Micro. 14, 456-460 (1995).

Yamada, Y. et al, The phylogenetic relationships of species of the Genus *Dekkera* van der Walt based on the partial sequences of 18S and 26S ribosomal RNAs (saccharomycetaceae). Biosci. Biotech. Biochem. 58, 1803-1808 (1994).

Kosse, D. et al, Identification of yoghurt-spoiling yeasts with 18S rRNA-targeted oligonucleotide probes. Systematic And Applied Microbiology 20, 468-480 (1997).

Stender, H. et al, A new molecular method for simultaneous Identification and enumeration of *Brettanomyces* in wine. Abstracts Of The General Meeting Of The American Society For Microbiology 99, 516 (1999).

Wyder et al, A rapid method for Identification of yeasts from kefyr at species level. Milchwissenschaft, DE, VV GMBH 52, 327-330 (1997).

Amann, R.I. et al, Identification of Individual prokaryotic cells by using enzyme-labeled, rRNA-targeted oligonucleotide probes. Appl. & Environ. Microbiology 58, 3007-3011 (1992).

Bergmann, F. et al, Solid phase synthesis of directly linked PNA-DNA-hybrids. Tet. Lett. 36, 6823-6826 (1995).

Boekhout, T. et al, Phylogeny of the yeast genera *Hanseniaspora* (anamorph *Kloeckera*), *Dekkera* (anamorph *Brettanomyces*), and *Eeniella* as Inferred from partial 26S ribosomal DNA nucleotide sequences. Intl. J. Systematic Bacteriology 44, 781-786 (1994).

Egholm, M. et al, PNA hybridizes to complementary oligonucleotides obeying the Watson-Crick hydrogen-bonding rules. Nature 365, 566-568 (1993).

Fugelsang, K.C. et al, Wine Microbiology Chapman & Hall, NY (1997).

Gildea, B.D. et al, PNA solubility enhancers. Tet. Lett. 39, 7255-7258 (1998).

Good, L. et al, Progress In developing PNA as a gene-targeted drug. Antisense & Nucl. Acid Drug Dev 7, 431-437 (1997).

Haaima, G. et al, Peptide nucleic acids (PNAs) containing thymine monomers derived from chiral amin acids: hybridization and solubility properties of D-Lysine PNA. Angew. Chem. Int. Ed. Engl. 35, 1939-1942 (1996).

Kurtzman, C.P. et al, Identification and phylogeny of ascomycetous yeasts from analysis of nuclea larg subunit (26S) ribosomal DNA partial sequences. Antonie van Leewenhoek 73, 331-371 (1998).

Lesnick, E. et al, Triplex formation between DNA and mixed purine-pyrimidine PNA analog with lysines In backbone. Nucleosides & Nucleotides 16, 1775-1779 (1997).

Nielsen, P.E. et al, Peptide nucleic acids (PNAs): potential anti-sense and anti-gene agents. Anti-Cancer Drug Design 8, 53-63 (1993).

Smith, M.T., The Yeasts—A Taxonomic Study (eds. C.P. Kurtzman & J.W. Fell), Elsevier Science B.V. Amsterdam, The Netherlands, pp. 174-177 and pp. 450-453 (1998).

Tomac, S. et al, Ionic effects on the stability and conformation of peptide nucleic acid complexes. J. Am. Chem. Soc. 118, 5544-5552 (1996).

Weiler, J. et al, Hybridisation based DNA screening on peptide nucleic acid (PNA) oligomer arrays. Nucl. Acids Res. 25, 2792-2799 (1997).

* cited by examiner

A B C D E F G H I J K L M N

EuUni 1

Bre04

Bre05

Bre14

Bre20

Wine #28, 1µl and 10µl duplicates, grown 44 hours, probed Bre14

Wine #30, 1µl and 10µl duplicates, grown 24 hours, probed Bre14

Wine #2, 10 fold dilutions, triplicates, samples grown 3 days, probed with Bre14.

SEQUENCE LISTING

<160> NUMBER OF SEQ ID NOS: 4

<210> SEQ ID NO 1
<211> LENGTH: 2058
<212> TYPE: DNA
<213> ORGANISM: homo sapiens

<400> SEQUENCE: 1

```
atgctctggt tctccggcgt cggggctctg gctgagcgtt actgccgccg ctcgcctggg      60
attacgtgct gcgtcttgct gctactcaat tgctcggggg tccccatgtc tctggcttcc     120
tccttcttga caggttctgt tgcaaaatgt gaaaatgaag gtgaagtcct ccagattcca     180
tttatcacag acaaccettg cataatgtgt gtctgcttga acaaggaagt gacatgtaag     240
agagagaagt gccccgtgct gtcccgagac tgtgccctgg ccatcaagca gagggagcc     300 tgttgtgaac agtgcaaagg ttgcacctat gaaggaaata cctataacag ctccttcaaa     360
tggcagagcc cggctgagcc ttgtgttcta cgccagtgcc aggagggtgt tgtcacagag     420
tctggggtgc gctgtgttgt tcattgtaaa aaccctttgg agcatctggg aatgtgctgc     480
cccacatgtc caggctgtgt gtttgagggt gtgcagtatc aagaagggga ggaattcag     540 ccagaaggaa gcaaatgtac caagtgttcc tgcactggag gcaggacaca atgtgtgaga     600
gaagtctgtc ccattctctc ctgtcccag caccttagtc acatacccc aggacagtgc      660 tgccccaaat gtttgggtca gaggaaagtg tttgacctcc cttttgggag ctgcctcttt     720
cgaagtgatg tttatgacaa tggatcctca tttctgtacg ataactgcac agcttgtacc     780
tgcagggact ctactgtggt ttgcaagagg aagtgctccc accctggtgg ctgtgaccaa     840
ggccaggagg gctgttgtga agagtgcctc ctacgagtgc ccccagaaga catcaaagta     900
tgcaaatttg gcaacaagat tttccaggat ggagagatgt ggtcctctat caattgtacc     960
atctgtgctt gtgtgaaagg caggacggag tgtcgcaata agcagtgcat tcccatcagt    1020
agctgcccac agggcaaaat tctcaacaga aaaggatgct gtcctatttg cactgaaaag    1080
cccggcgttt gcacggtgtt tggagatccc cactacaaca cttttgacgg tcggacattt    1140
aactttcagg ggacgtgtca gtacgttttg acaaaagact gctcctcccc tgcctcgccc    1200
ttccaggtgc tggtgaagaa cgacgcccgc cggacacgct ccttctcgtg gaccaagtcg    1260
gtggagctgg tgctgggcga gagcagggtc agcctgcagc agcacctcac cgtgcgctgg    1320
aacggctcgc gcatcgcgct ccctgccgc gcgccacact tccacatcga cctggatggc    1380 taccttcttga aagtgaccac caaagcaggt ttggaaatat cttgggatgg agacagtttt    1440
gtagaagtca tggctgcgcc tcatctcaag ggcaagctct gtggtctttg tggcaactac    1500
```

-continued

```
aatggacata aacgtgatga cttaattggt ggagatggaa acttcaagtt tgatgtggat    1560
gactttgctg aatcttggag ggtggagtcc aatgagttct gcaacagacc tcagagaaag    1620
ccagtgcctg aactgtgtca agggacagtc aaggtaaagc tccgggccca tcgagaatgc    1680
caaaagctca atcctggga gtttcagacc tgccactcga ctgtggacta cgccactttc     1740
taccggtcct gtgtgacaga catgtgtgaa tgtccagtcc ataaaaactg ttattgcgag    1800 tcattttttgg catataccccg ggcctgccag agagagggca tcaaagtcca ctgggagcct   1860
cagcagaatt gtgcagccac ccagtgtaag catggtgctg tgtacgatac ctgtggtccg    1920
ggatgtatca agacctgtga caactggaat gaaattggtc catgcaacaa gccgtgcgtt    1980
gctgggtgcc actgtccagc aaacttggtc cttcacaagg gaaggtgcat caagccagtc    2040
ctttgtcccc agcggtga                                                  2058
```

<210> SEQ ID NO 2
<211> LENGTH: 685
<212> TYPE: PRT
<213> ORGANISM: homo sapiens

<400> SEQUENCE: 2

```
Met Leu Trp Phe Ser Gly Val Gly Ala Leu Ala Glu Arg Tyr Cys Arg
 1               5                  10                  15

Arg Ser Pro Gly Ile Thr Cys Cys Val Leu Leu Leu Asn Cys Ser
            20                  25                  30

Gly Val Pro Met Ser Leu Ala Ser Ser Phe Leu Thr Gly Ser Val Ala
        35                  40                  45

Lys Cys Glu Asn Glu Gly Glu Val Leu Gln Ile Pro Phe Ile Thr Asp
    50                  55                  60

Asn Pro Cys Ile Met Cys Val Cys Leu Asn Lys Glu Val Thr Cys Lys
65                  70                  75                  80

Arg Glu Lys Cys Pro Val Leu Ser Arg Asp Cys Ala Leu Ala Ile Lys
                85                  90                  95

Gln Arg Gly Ala Cys Cys Glu Gln Cys Lys Gly Cys Thr Tyr Glu Gly
            100                 105                 110

Asn Thr Tyr Asn Ser Ser Phe Lys Trp Gln Ser Pro Ala Glu Pro Cys
        115                 120                 125

Val Leu Arg Gln Cys Gln Glu Gly Val Val Thr Glu Ser Gly Val Arg
    130                 135                 140

Cys Val Val His Cys Lys Asn Pro Leu Glu His Leu Gly Met Cys Cys
145                 150                 155                 160

Pro Thr Cys Pro Gly Cys Val Phe Glu Gly Val Gln Tyr Gln Glu Gly
                165                 170                 175

Glu Glu Phe Gln Pro Glu Gly Ser Lys Cys Thr Lys Cys Ser Cys Thr
            180                 185                 190

Gly Gly Arg Thr Gln Cys Val Arg Glu Val Cys Pro Ile Leu Ser Cys
        195                 200                 205

Pro Gln His Leu Ser His Ile Pro Pro Gly Gln Cys Cys Pro Lys Cys
    210                 215                 220

Leu Gly Gln Arg Lys Val Phe Asp Leu Pro Phe Gly Ser Cys Leu Phe
225                 230                 235                 240

Arg Ser Asp Val Tyr Asp Asn Gly Ser Ser Phe Leu Tyr Asp Asn Cys
                245                 250                 255

Thr Ala Cys Thr Cys Arg Asp Ser Thr Val Val Cys Lys Arg Lys Cys
            260                 265                 270
```

```
Ser His Pro Gly Gly Cys Asp Gln Gly Gln Glu Gly Cys Cys Glu
    275                 280                 285
Cys Leu Leu Arg Val Pro Pro Glu Asp Ile Lys Val Cys Lys Phe Gly
    290                 295                 300
Asn Lys Ile Phe Gln Asp Gly Glu Met Trp Ser Ser Ile Asn Cys Thr
305                 310                 315                 320
Ile Cys Ala Cys Val Lys Gly Arg Thr Glu Cys Arg Asn Lys Gln Cys
                325                 330                 335
Ile Pro Ile Ser Ser Cys Pro Gln Gly Lys Ile Leu Asn Arg Lys Gly
            340                 345                 350
Cys Cys Pro Ile Cys Thr Glu Lys Pro Gly Val Cys Thr Val Phe Gly
        355                 360                 365
Asp Pro His Tyr Asn Thr Phe Asp Gly Arg Thr Phe Asn Phe Gln Gly
    370                 375                 380
Thr Cys Gln Tyr Val Leu Thr Lys Asp Cys Ser Ser Pro Ala Ser Pro
385                 390                 395                 400
Phe Gln Val Leu Val Lys Asn Asp Ala Arg Arg Thr Arg Ser Phe Ser
                405                 410                 415
Trp Thr Lys Ser Val Glu Leu Val Leu Gly Glu Ser Arg Val Ser Leu
            420                 425                 430
Gln Gln His Leu Thr Val Arg Trp Asn Gly Ser Arg Ile Ala Leu Pro
        435                 440                 445
Cys Arg Ala Pro His Phe His Ile Asp Leu Asp Gly Tyr Leu Leu Lys
    450                 455                 460
Val Thr Thr Lys Ala Gly Leu Glu Ile Ser Trp Asp Gly Asp Ser Phe
465                 470                 475                 480
Val Glu Val Met Ala Ala Pro His Leu Lys Gly Lys Leu Cys Gly Leu
                485                 490                 495
Cys Gly Asn Tyr Asn Gly His Lys Arg Asp Asp Leu Ile Gly Gly Asp
            500                 505                 510
Gly Asn Phe Lys Phe Asp Val Asp Asp Phe Ala Glu Ser Trp Arg Val
        515                 520                 525
Glu Ser Asn Glu Phe Cys Asn Arg Pro Gln Arg Lys Pro Val Pro Glu
    530                 535                 540
Leu Cys Gln Gly Thr Val Lys Val Lys Leu Arg Ala His Arg Glu Cys
545                 550                 555                 560
Gln Lys Leu Lys Ser Trp Glu Phe Gln Thr Cys His Ser Thr Val Asp
                565                 570                 575
Tyr Ala Thr Phe Tyr Arg Ser Cys Val Thr Asp Met Cys Glu Cys Pro
            580                 585                 590
Val His Lys Asn Cys Tyr Cys Glu Ser Phe Leu Ala Tyr Thr Arg Ala
        595                 600                 605
Cys Gln Arg Glu Gly Ile Lys Val His Trp Glu Pro Gln Gln Asn Cys
    610                 615                 620
Ala Ala Thr Gln Cys Lys His Gly Ala Val Tyr Asp Thr Cys Gly Pro
625                 630                 635                 640
Gly Cys Ile Lys Thr Cys Asp Asn Trp Asn Glu Ile Gly Pro Cys Asn
                645                 650                 655
Lys Pro Cys Val Ala Gly Cys His Cys Pro Ala Asn Leu Val Leu His
            660                 665                 670
Lys Gly Arg Cys Ile Lys Pro Val Leu Cys Pro Gln Arg
        675                 680                 685
```

-continued

<210> SEQ ID NO 3
<211> LENGTH: 1884
<212> TYPE: DNA
<213> ORGANISM: homo sapiens

<400> SEQUENCE: 3

| atgctctggt | tctccggcgt | cggggctctg | gctgagcgtt | actgccgccg | ctcgcctggg | 60 |
| attacgtgct | gcgtcttgct | gctactcaat | tgctcggggg | tccccatgtc | tctggcttcc | 120 |
| tccttcttga | caggttctgt | tgcaaaatgt | gaaaatgaag | gtgaagtcct | ccagattcca | 180 |
| tttatcacag | acaacccttg | cataatgtgt | gtctgcttga | caaggaagt | gacatgtaag | 240 |
| agagagaagt | gccccgtgct | gtcccgagac | tgtgccctgg | ccatcaagca | gaggggagcc | 300 |
| tgttgtgaac | agtgcaaagg | ttgcacctat | gaaggaaata | cctataacag | ctccttcaaa | 360 |
| tggcagagcc | cggctgagcc | ttgtgttcta | cgccagtgcc | aggagggtgt | tgtcacagag | 420 |
| tctggggtgc | gctgtgttgt | tcattgtaaa | aacccttggg | agcatctggg | aatgtgctgc | 480 |
| cccacatgtc | caggctgtgt | gtttgagggt | gtgcagtatc | aagaagggga | ggaatttcag | 540 |
| ccagaaggaa | gcaaatgtac | caagtgttcc | tgcactggag | gcaggacaca | atgtgtgaga | 600 |
| gaagtctgtc | ccattctctc | ctgtccccag | caccttagtc | atacccccc | aggacagtgc | 660 |
| tgccccaaat | gtttgggtca | gaggaaagtg | tttgacctcc | cttttgggag | ctgcctcttt | 720 |
| cgaagtgatg | tttatgacaa | tggatcctca | tttctgtacg | ataactgcac | agcttgtacc | 780 |
| tgcagggact | ctactgtggt | ttgcaagagg | aagtgctccc | accctggtgg | ctgtgaccaa | 840 |
| ggccaggagg | gctgttgtga | agagtgcctc | ctacgagtgc | ccccagaaga | catcaaagta | 900 |
| tgcaaatttg | gcaacaagat | tttccaggat | ggagagatgt | ggtcctctat | caattgtacc | 960 |
| atctgtgctt | gtgtgaaagg | caggacggag | tgtcgcaata | gcagtgcat | cccatcagt | 1020 |
| agctgcccac | aggtgctggt | gaagaacgac | gcccgccgga | cacgctcctt | ctcgtggacc | 1080 |
| aagtcggtgg | agctggtgct | gggcgagagc | agggtcagcc | tgcagcagca | cctcaccgtg | 1140 |
| cgctggaacg | gctcgcgcat | cgcgctcccc | tgccgcgcgc | cacacttcca | catcgacctg | 1200 |
| gatggctacc | tcttgaaagt | gaccaccaaa | gcaggtttgg | aaatatcttg | ggatggagac | 1260 |
| agttttgtag | aagtcatggc | tgcgcctcat | ctcaagggca | agctctgtgg | tctttgtggc | 1320 |
| aactacaatg | gacataaacg | tgatgactta | attggtggag | atggaaactt | caagtttgat | 1380 |
| gtggatgact | tgctgaatc | ttggagggtg | gagtccaatg | agttctgcaa | cagacctcag | 1440 |
| agaaagccag | tgcctgaact | gtgtcaaggg | acagtcaagg | taaagctccg | ggcccatcga | 1500 |
| gaatgccaaa | agctcaaatc | ctgggagttt | cagacctgcc | actcgactgt | ggactacgcc | 1560 |
| actttctacc | ggtcctgtgt | gacagacatg | tgtgaatgtc | cagtccataa | aaactgttat | 1620 |
| tgcgagtcat | ttttggcata | tacccgggcc | tgccagagag | agggcatcaa | agtccactgg | 1680 |
| gagcctcagc | agaattgtgc | agccacccag | tgtaagcatg | gtgctgtgta | cgatacctgt | 1740 |
| ggtccgggat | gtatcaagac | ctgtgacaac | tggaatgaaa | ttggtccatg | caacaagccg | 1800 |
| tgcgttgctg | ggtgccactg | tccagcaaac | ttggtccttc | acaagggaag | gtgcatcaag | 1860 |
| ccagtccttt | gtccccagcg | gtga | | | | 1884 |

<210> SEQ ID NO 4
<211> LENGTH: 627
<212> TYPE: PRT
<213> ORGANISM: homo sapiens

<400> SEQUENCE: 4

-continued

```
Met Leu Trp Phe Ser Gly Val Gly Ala Leu Ala Glu Arg Tyr Cys Arg
 1               5                  10                  15

Arg Ser Pro Gly Ile Thr Cys Cys Val Leu Leu Leu Asn Cys Ser
            20                  25                  30

Gly Val Pro Met Ser Leu Ala Ser Ser Phe Leu Thr Gly Ser Val Ala
            35                  40                  45

Lys Cys Glu Asn Glu Gly Glu Val Leu Gln Ile Pro Phe Ile Thr Asp
 50                  55                  60

Asn Pro Cys Ile Met Cys Val Cys Leu Asn Lys Glu Val Thr Cys Lys
 65                  70                  75                  80

Arg Glu Lys Cys Pro Val Leu Ser Arg Asp Cys Ala Leu Ala Ile Lys
                85                  90                  95

Gln Arg Gly Ala Cys Cys Glu Gln Cys Lys Gly Cys Thr Tyr Glu Gly
                100                 105                 110

Asn Thr Tyr Asn Ser Ser Phe Lys Trp Gln Ser Pro Ala Glu Pro Cys
            115                 120                 125

Val Leu Arg Gln Cys Gln Glu Gly Val Val Thr Glu Ser Gly Val Arg
    130                 135                 140

Cys Val Val His Cys Lys Asn Pro Leu Glu His Leu Gly Met Cys Cys
145                 150                 155                 160

Pro Thr Cys Pro Gly Cys Val Phe Glu Gly Val Gln Tyr Gln Glu Gly
                165                 170                 175

Glu Glu Phe Gln Pro Glu Gly Ser Lys Cys Thr Lys Cys Ser Cys Thr
            180                 185                 190

Gly Gly Arg Thr Gln Cys Val Arg Glu Val Cys Pro Ile Leu Ser Cys
        195                 200                 205

Pro Gln His Leu Ser His Ile Pro Pro Gly Gln Cys Cys Pro Lys Cys
    210                 215                 220

Leu Gly Gln Arg Lys Val Phe Asp Leu Pro Phe Gly Ser Cys Leu Phe
225                 230                 235                 240

Arg Ser Asp Val Tyr Asp Asn Gly Ser Ser Phe Leu Tyr Asp Asn Cys
                245                 250                 255

Thr Ala Cys Thr Cys Arg Asp Ser Thr Val Val Cys Lys Arg Lys Cys
            260                 265                 270

Ser His Pro Gly Gly Cys Asp Gln Gly Gln Glu Gly Cys Cys Glu Glu
        275                 280                 285

Cys Leu Leu Arg Val Pro Pro Glu Asp Ile Lys Val Cys Lys Phe Gly
    290                 295                 300

Asn Lys Ile Phe Gln Asp Gly Glu Met Trp Ser Ser Ile Asn Cys Thr
305                 310                 315                 320

Ile Cys Ala Cys Val Lys Gly Arg Thr Glu Cys Arg Asn Lys Gln Cys
                325                 330                 335

Ile Pro Ile Ser Ser Cys Pro Gln Val Leu Val Lys Asn Asp Ala Arg
            340                 345                 350

Arg Thr Arg Ser Phe Ser Trp Thr Lys Ser Val Glu Leu Val Leu Gly
        355                 360                 365

Glu Ser Arg Val Ser Leu Gln Gln His Leu Thr Val Arg Trp Asn Gly
    370                 375                 380

Ser Arg Ile Ala Leu Pro Cys Arg Ala Pro His Phe His Ile Asp Leu
385                 390                 395                 400

Asp Gly Tyr Leu Leu Lys Val Thr Thr Lys Ala Gly Leu Glu Ile Ser
                405                 410                 415

Trp Asp Gly Asp Ser Phe Val Glu Val Met Ala Ala Pro His Leu Lys
```

-continued

```
              420                 425                 430
Gly Lys Leu Cys Gly Leu Cys Gly Asn Tyr Asn Gly His Lys Arg Asp
        435                 440                 445

Asp Leu Ile Gly Gly Asp Gly Asn Phe Lys Phe Asp Val Asp Asp Phe
    450                 455                 460

Ala Glu Ser Trp Arg Val Glu Ser Asn Glu Phe Cys Asn Arg Pro Gln
465                 470                 475                 480

Arg Lys Pro Val Pro Glu Leu Cys Gln Gly Thr Val Lys Val Lys Leu
                485                 490                 495

Arg Ala His Arg Glu Cys Gln Lys Leu Lys Ser Trp Glu Phe Gln Thr
            500                 505                 510

Cys His Ser Thr Val Asp Tyr Ala Thr Phe Tyr Arg Ser Cys Val Thr
        515                 520                 525

Asp Met Cys Glu Cys Pro Val His Lys Asn Cys Tyr Cys Glu Ser Phe
    530                 535                 540

Leu Ala Tyr Thr Arg Ala Cys Gln Arg Glu Gly Ile Lys Val His Trp
545                 550                 555                 560

Glu Pro Gln Gln Asn Cys Ala Ala Thr Gln Cys Lys His Gly Ala Val
                565                 570                 575

Tyr Asp Thr Cys Gly Pro Gly Cys Ile Lys Thr Cys Asp Asn Trp Asn
            580                 585                 590

Glu Ile Gly Pro Cys Asn Lys Pro Cys Val Ala Gly Cys His Cys Pro
        595                 600                 605

Ala Asn Leu Val Leu His Lys Gly Arg Cys Ile Lys Pro Val Leu Cys
    610                 615                 620

Pro Gln Arg
625
```

METHODS FOR THE DETECTION, IDENTIFICATION, AND/OR ENUMERATION OF YEAST, PARTICULARLY IN WINE

CROSS REFERENCE TO RELATED APPLICATIONS

This application claims the benefit of U.S. Provisional Patent Application Ser. No. 60/139,212 filed on Jun. 15, 1999.

STATEMENT REGARDING FEDERALLY SPONSORED RESEARCH OR DEVELOPMENT

The US Government has certain rights in this invention as provided for by the terms of the Cooperative Research and Development Agreement (CRADA) No. 58-3K95-8-631 by and between Boston Probes, Inc. and the United States Department of Agriculture.

BACKGROUND OF THE INVENTION

1. Field of the Invention

This invention is related to the field of probe-based detection, analysis and quantitation of yeast and particularly *Dekkera bruxellensis* (a.k.a. *Brettanomyces*) in wine. More specifically, this invention relates to novel probes, probe sets, methods and kits that can be used to detect, identify and/or quantitate (enumerate) one or more yeast in a sample and particularly those organisms that spoil wine.

2. Description of the Related Art

Nucleic acid hybridization is a fundamental process in molecular biology. Probe-based assays are useful in the detection, identification, quantitation and analysis of nucleic acids. Nucleic acid probes have long been used to analyze samples for the presence of nucleic acid from yeast, eucarya, fungi, virus or other organisms and are also useful in examining genetically-based disease states or clinical conditions of interest. Nonetheless, probe-based assays have been slow to achieve commercial success. This lack of commercial success is, at least partially, the result of difficulties associated with probe stability, specificity, sensitivity and reliability.

Despite its name, Peptide Nucleic Acid (PNA) is neither a peptide, a nucleic acid nor is it an acid. Peptide Nucleic Acid (PNA) is a non-naturally occurring polyamide that can hybridize to nucleic acid (DNA and RNA) with sequence specificity (See: U.S. Pat. No. 5,539,082 and Egholm et al., *Nature* 365: 566–568 (1993)). Being a non-naturally occurring molecule, unmodified PNA is not known to be a substrate for the enzymes that are known to degrade peptides or nucleic acids. Therefore, PNA should be stable in biological samples, as well as have a long shelf-life. Unlike nucleic acid hybridization which is very dependent on ionic strength, the hybridization of a PNA with a nucleic acid is fairly independent of ionic strength and is favored at low ionic strength, conditions that strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.* 118:5544–5552 (1996)). Sequence discrimination is more efficient for PNA recognizing DNA than for DNA recognizing DNA (Egholm et al., *Nature, at p.* 566). However, the advantages in point mutation discrimination with PNA probes, as compared with DNA probes, in a hybridization assay, appears to be somewhat sequence dependent (Nielsen et al., *Anti-Cancer Drug Design* 8:53–63, (1993) and Weiler et al., *Nucl. Acids Res.* 25: 2792–2799 (1997)).

Though they hybridize to nucleic acid with sequence specificity (See: Egholm et al., *Nature*, at p. 567), PNAs have been slow to achieve commercial success at least partially due to cost, sequence specific properties/problems associated with solubility and self-aggregation (See: Bergman, F., Bannwarth, W. and Tam, S., *Tett. Lett.* 36:6823–6826 (1995), Haaima, G., Lohse, A., Buchardt, O. and Nielsen, P. E., *Angew. Chem. Int. Ed. Engl.* 35:1939–1942 (1996) and Lesnik, E., Hassman, F., Barbeau, J., Teng, K. and Weiler, K., *Nucleosides & Nucleotides* 16:1775–1779 (1997) at p 433, col. 1, ln. 28 through col. 2, ln. 3) as well as the uncertainty pertaining to non-specific interactions that might occur in complex systems such as a cell (See: Good, L. et al., *Antisense & Nucleic Acid Drug Development* 7:431–437 (1997)). However, problems associated with solubility and self-aggregation have recently been reduced or eliminated (See: Gildea et al., *Tett. Lett.* 39: 7255–7258 (1998)). Nevertheless, their unique properties clearly demonstrate that PNA is not the equivalent of a nucleic acid in either structure or function. Consequently, PNA probes need to be evaluated for performance and optimization to thereby confirm whether they can be used to specifically and reliably detect a particular nucleic acid target sequence, particularly when the target sequence exists in a complex sample such as a cell, tissue or organism.

DNA and PNA probes targeting rRNA have been used for the detection of bacteria (gonorrhoeae and mycobacteria) and eucarya by in situ hybridization (See: WO95/32305 (now U.S. Pat. No. 5,985,563), WO98/15648; and WO97/18325 (now U.S. Pat. No. 5,888,733) respectively). PNA probes have also been used to examine telomeres and repeat sequences by in-situ hybridization (See: WO97/14026). Methods for the linking of enzymes to both DNA and PNA probes are known in the art (See: WO99/41273). However, the use of enzyme-labeled DNA probes for the detection of yeast cells by in-situ hybridization has not yet been demonstrated (Amann, R. I., Zarda, B., Stahl, D. A. and Schleifer, K.-H., Identification of individual prokaryotic cells by using enzyme-labeled, rRNA-targeted oligonucleotide probes, *Applied and Environmental Microbiology*, 58: 3007–3011 (1992)) and Applicants are unaware of any attempts to use enzyme-labeled PNA probes to detect yeast by in-situ hybridization. The lack of examples of successful ISH assays utilizing enzyme linked probes likely results because of difficulties in getting such large molecules to pass through the cell membrane into the yeast cytoplasm.

Wine making is both a hobby as well as an established industry. The organism called *Brettanomyces* (ascosporic state of *Dekkera*) within the wine industry is a spoilage yeast causing 'mousiness'; an undesirable odor and taste. The nomenclature of *Brettanomyces* used within the field of wine enology is based on synonyms rather than on accepted specie names from the recently published taxonomy of the *Brettanomyces/Dekkera* species (See: Smith, M. T., The Yeasts A Taxonomic Study (eds. C. P. Kurtzman & J. W. Fell), *Elsevier Science* B. V., Amsterdam, The Netherlands (1998), pp. 174–177 and pp. 450–453). The lack of proper characterization of the organism that causes wine spoilage has complicated the nucleobase sequence design of specific probes targeting the spoilage organism, since available rDNA sequence information (See: Kurtzman, C. P. and C. J. Robnett., Identification and phylogeny of ascomycetous yeasts from analysis of nuclear large subunit (26S) ribosomal DNA partial sequences, Antonie van Leeuwenhoek 73: 331–371 (1998), Boekhout, T., Kurtzman, C. P., O'Donell, K. and Smith, M. T., Phylogeny of the yeast genera *Hanseniaspora* (anamorph *Kloeckera*), *Dekkera* (anamorph *Brettanomyces*), and *Eeniella* as inferred from partial 26S ribosomal DNA nucleotide sequences, *International Journal of Systematic Bacteriology,* 44: 781–786 (1994)) is based on the five accepted species of *Brettanomyces/Dekkera* (*Dekkera anomala, Dekkera bruxellensis, Brettanomyces custersianus, Brettanomyces naardenensis, Brettanomyces nanus*). Therefore, it is not obvious what sequence information should be used to generate target sequences suitable for specific detection of the wine spoilage organism known in the wine industry as *Brettanomyces.*

Current methods for identification and enumeration of *Brettanomyces* in wine takes 1–2 weeks and rely on growth occurring on a semi-selective culture medium followed by final identification from morphology and biochemical testing (See: Fugelsang, K. C., *Wine Microbiology* Chapman & Hall, NY (1997)). This process is very time consuming and relies on highly trained laboratory personal to perform the final identification. Faster methods are available for enumeration of organisms present in a sample but these methods lack the ability to identify or speciate the detected organisms. Because wine samples often contain non-spoilage yeasts, such as *Saccharomyces cerevisiae*, these methods are of limited usefulness. Because wine spoilage caused by *Brettanomyces* is a substantial concern for those who make wine, any methods, kits or compositions suitable for rapid, reliable and sensitive detection, identification and/or quantitation (enumerate) of *Brettanomyces* in wine would allow for more effective intervention in the wine making process and thereby improve product quality and/or reduce the costs of manufacture.

SUMMARY OF THE INVENTION

In one embodiment, this invention is directed to an enzyme-linked probe suitable for use in an in-situ hybridization assay and further characterized in that it comprises a probing nucleobase sequence directed to a target sequence within a yeast. Exemplary enzymes suitable as detectable labels are described below. The probe may comprise a nucleic acid or non-nucleic acid probing nucleobase sequence but preferably the probing nucleobase sequence is of the non-nucleic acid type and most preferably the probe is a PNA oligomer. The probing nucleobase sequence of the enzyme-linked probe is designed to detect specific yeasts, genus of yeasts or even be designed for the universal detection of all yeasts.

In another embodiment, this invention is also directed to probes, probe sets and kits (containing probes and other reagents or compositions that are selected to perform an assay or otherwise simplify the performance of an assay) suitable for the detection of the presence, absence or number of *Dekkera/Brettanomyces* yeast in a sample and particularly *Dekkera bruxellensis* (*Brettanomyces*). The probes are preferably, but not necessarily, non-nucleic acid probes and most preferably PNA probes. The preferred probing nucleobase sequence of the probes of this invention, that are suitable for detecting, identifying or quantitating *Dekkera/Brettanomyces* yeast, are listed in Table 1, below. In preferred embodiments, probes are organized into a set or kit that is suitable for the specific detection, identification and/or quantitation of *Dekkera/Brettanomyces* yeast and in particular *Dekkera bruxellensis* (*Brettanomyces*) yeast present in a sample. In another embodiment, the probe set or kit is designed to detect, identify or quantitate *Dekkera/Brettanomyces* yeast as well as other organisms of interest that may be present in the sample. When the assay is designed for multi-organism analysis, preferably a multiplex format is used so that the presence or quantity of each organism of interest can be individually, but simultaneously, identified and/or scored. In the most preferred embodiment of this invention, the probes, probe sets or kits are applied to the analysis of wine.

In yet another embodiment, this invention is generally directed to a method for the detection, identification or quantitation (enumeration) of yeast using enzyme-linked probes (nucleic acid or non-nucleic acid) by an in-situ hybridization (ISH) assay. According to the method, a sample containing one or more species of yeast is contacted with a yeast specific enzyme-linked probe, under suitable in-situ hybridization conditions. The enzyme-linked probe will hybridize to the target sequence of the yeast, if present in the in-situ assay, and the activity of the enzyme can be used to detect, identify or quantitate the yeast present in the sample as correlated with the formation and presence of the probe/target sequence hybrid. In a preferred embodiment, the target sequence is a rRNA sequence. Exemplary enzymes suitable as detectable labels are described below. The probe may comprise a nucleic acid or non-nucleic acid probing nucleobase sequence but preferably the probing nucleobase sequence is of the non-nucleic acid type and most preferably it is a peptide nucleic acid. The nucleobase sequence of the enzyme-linked probe can be designed to detect specific yeasts, genius of yeasts or even be designed for the universal for the detection of all yeasts.

This invention is still further directed to a method suitable for detecting, identifying or quantitating *Dekkera/Brettanomyces* yeast in a sample and particularly *Dekkera bruxellensis* (*Brettanomyces*). The method comprises contacting the sample with one or more probes that hybridize to nucleic acid specific to *Dekkera/Brettanomyces* yeast, or more particularly to nucleic acid specific to *Dekkera bruxellensis* (*Brettanomyces*), wherein the general characteristics and preferred probing nucleobase sequences of suitable probes are described herein. Preferably, the target sequence of the probe is a rRNA sequence.

According to the method, the presence, absence or number of yeast in the sample are then detected, identified or quantitated. Detection, identification and/or quantitation is made possible by correlating the hybridization, under suitable hybridization conditions, of the probing nucleobase sequence of a probe to the target sequence to thereby determine the presence, absence or number of yeast (*Dekkera/Brettanomyces* yeast and particularly *Dekkera bruxellensis* (*Brettanomyces*)) present in the sample. Preferably, but not necessarily, the method is performed as an in-situ hybridization assay under suitable in-situ hybridization conditions. In preferred embodiments, the probe is labeled with an enzyme and most preferably the enzyme is soy bean peroxidase. In the most preferred embodiment, the method is applied to the analysis of wine.

By utilizing confirmed spoilage samples from wineries, the probes, probe sets, methods and kits of this invention have, by in-situ analysis, been demonstrated to be very specific for species of the *Dekkera/Brettanomyces* yeast and particularly *Dekkera bruxellensis* (*Brettanomyces*); identified as the agent causing wine spoilage. Applicants believe this to be the first successful example of the use of an enzyme-linked probe (PNA or nucleic acid) for the in-situ analysis of yeast cells. By "specific" we mean that the preferred probes of this invention were demonstrated to detect target sequences within the rRNA of *Dekkera/Brettanomyces* yeast and particularly *Dekkera bruxellensis* (*Brettanomyces*) without substantial cross reaction with non-target yeasts commonly found in wine. Moreover, the assays described herein are rapid (the entire assay can be performed in 2 days or less as compared with 2 weeks for conventional assays wherein extensive incubation is required for colony generation) with the probe hybridization requiring as little as 30 minutes. Moreover, the assays and assay methods are sensitive, reliable and generally applicable to the many different probes of significantly different sequence variation (See: Table 3).

The probes, probe sets, methods and kits of this invention are particularly useful for the detection of yeast in food, pharmaceutical products, personal care products, dairy products as well as environmental and/or clinical samples. More preferably, they are used in the analysis of beverages including soda, bottled water, fruit juice, beer or liquor products and most preferably Applicants have demonstrated the utility of the probes of this invention for the analysis of *Dekkera/Brettanomyces* yeast wine. Suitable probes, probe sets, methods and kits will be particularly useful for the analysis of raw materials, equipment, products or processes used to manufacture or store of food, pharmaceutical products, personal care products, dairy products, environmental and clinical samples or beverages including soda, bottled water, fruit juice, beer or liquor products and most preferably wine. In particular, the probes, probe sets, methods and kits of this invention are particularly useful for the detection of *Dekkera/Brettanomyces* yeast and in particular, *Dekkera bruxellensis* (*Brettanomyces*) in wineries and breweries.

DESCRIPTION OF THE PREFERRED EMBODIMENTS OF THE INVENTION

Figure 1:
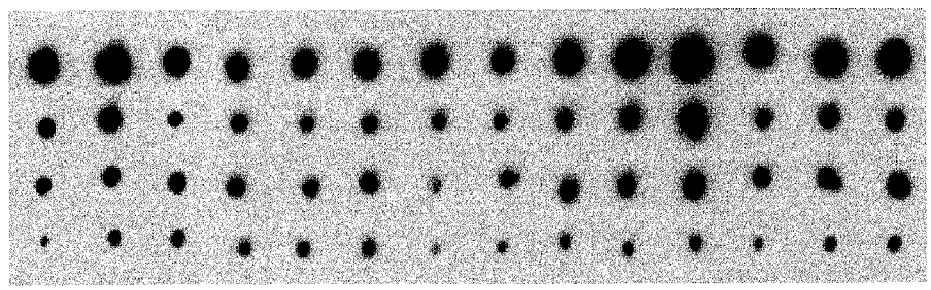
FIG. 1 comprises five panels that are electronic images of the X-ray film of dot blot assays (nylon membrane) used to examine the specificity of a universal SBP labeled PNA yeast probe (EuUni01; included as a control) and four SBP labeled PNA probes (SBP-BRE04, SBP-BRE05, SBP-BRE14 and SBP-BRE20) designed to be specific to the rRNA of one or more species of *Dekkera/Brettanomyces* yeast including *Dekkera bruxellensis* (*Brettanomyces*).
Figure 1:
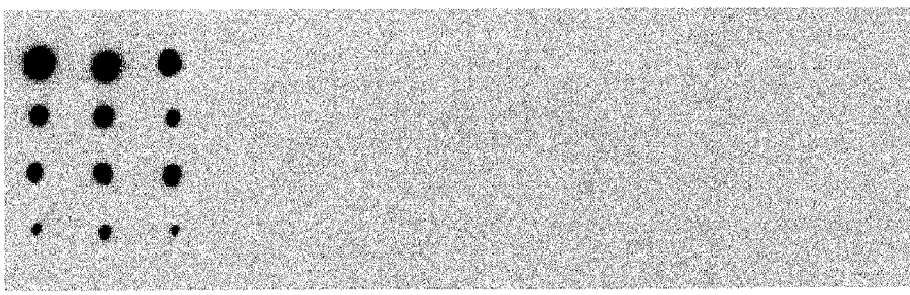
Figure 1:
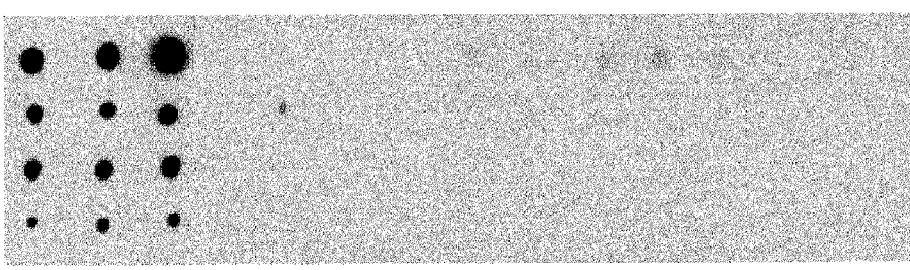
Figure 1:
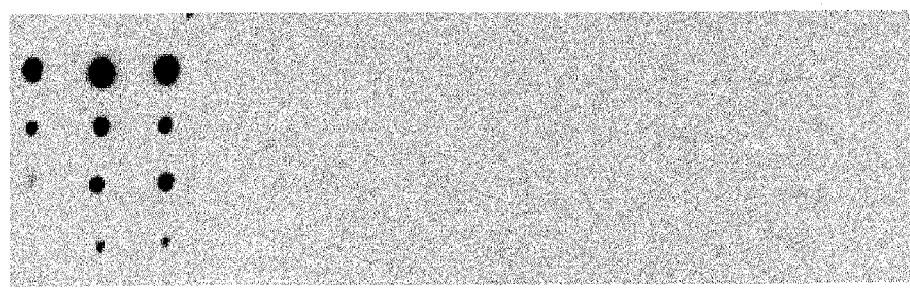
Figure 1:
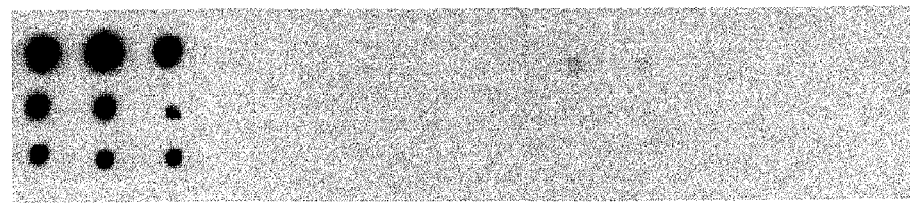

1. Definitions:
    a. As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.
    b. As used herein, the term "nucleobase sequence" means any segment of a polymer that comprises nucleobase containing subunits. Non-limiting examples of suitable polymers or polymers segments include oligonucleotides, oligoribonucleotides, peptide nucleic acids, nucleic acid analogs, nucleic acid mimics or chimeras.
    c. As used herein, the term "target sequence" means the nucleic acid nucleobase sequence of a specific yeast that is to be detected in an assay and to which at least a portion of the probing nucleobase sequence of the yeast specific probe is designed to hybridize, or a DNA or RNA copy thereof.
    d. As used herein the term "nucleic acid probe" means a probe comprising a probing nucleobase sequence that is designed to hybridize to at least a portion of the target sequence wherein the probing nucleobase sequence of said probe is further characterized in that it comprises a charged sugar phosphate backbone. Non-limiting examples of nucleic acid probes include oligodeoxynucleotides and oligoribonucleotides and charged analogs thereof.
    e. As used herein, the term "non-nucleic acid probe" means a probe comprising a probing nucleobase sequence that is designed to hybridize to at least a portion of the target sequence wherein the probing nucleobase sequence of said probe is further characterized in that it comprises a backbone that is not a charged sugar-phosphate backbone. A preferred non-limiting example of a non-nucleic acid probe is a peptide nucleic acid (PNA) probe.
    f. As used herein, the term "peptide nucleic acid" or "PNA" means as any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610 and 5,986,053; all of which are herein incorporated by reference. The term "peptide nucleic acid" or "PNA" shall also apply to polymers comprising two or more subunits of those nucleic acid mimics described in the following publications: Diderichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 1 1:5 55–560 (1997); Petersen et al., *Bioorg. Med. Chem. Lett.* 6: 793–796 (1996); Diederichsen, U., *Bioorganic & Med. Chem. Lett.,* 8: 165–168 (1998); Cantin et al., *Tett. Lett.,* 38: 4211–4214 (1997); Ciapetti et al., *Tetrahedron,* 53: 1167–1176 (1997); Lagriffoule et al., *Chem. Eur. J.,* 3: 912–919 (1997) and the Peptide-Based Nucleic Acid Mimics (PENAMs) of Shah et al. as disclosed in WO96/04000.

In preferred embodiments, a PNA is a polymer comprising two or more subunits of the formula:

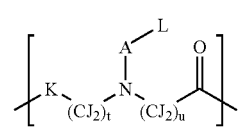

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms that may optionally contain a heteroatom or a substituted or unsubstituted aryl group. Each A is selected from the group consisting of a single bond, a group of the formula; —(CJ$_2$)$_s$— and a group of the formula; —(CJ$_2$)$_s$C(O)—, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

g. As used herein, the terms "label" and "detectable moiety" shall be interchangeable and refer to moieties that can be attached to a nucleic acid probe, a non-nucleic acid probe, a PNA probe, an antibody or an antibody fragment to thereby render the probe, antibody or antibody fragment detectable by an instrument or method.

h. As used herein, the term "chimera" or "chimeric oligomer" means an oligomer comprising two or more linked subunits that are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.

i. As used herein, the term "linked polymer" means a polymer comprising two or more polymer segments that are linked by a linker. The polymer segments that are linked to form the linked polymer are selected from the group consisting of an oligodeoxynucleotide, an oligoribonucleotide, a peptide, a polyamide, a peptide nucleic acid (PNA) and a chimera.

2. Description

I. General:

PNA Synthesis:

Methods for the chemical assembly of PNAs are well known (See: U.S. Pat. Nos. 5,539,082, 5,527,675, 5,623,049, 5,714,331, 5,736,336, 5,773,571, 5,786,461, 5,837,459, 5,891,625, 5,972,610 and 5,986,053, all of which are herein incorporated by reference). Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus that is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling:

Preferred methods for labeling PNAs are described in WO98/24933, WO99/22018 WO99/21881, the examples section of this specification or are otherwise well known in the art of PNA synthesis. Specific methods for the synthesis of PNA-enzyme and DNA-enzyme conjugates is described in WO99/41273.

Labels:

Non-limiting examples of detectable moieties (labels) suitable for labeling nucleic acid or non-nucleic acid probes used in the practice of this invention would include chromophores, fluorochromes, spin labels, radioisotopes, enzymes, haptens and chemiluminescent compounds. Preferred haptens include 5(6)-carboxyfluorescein, 2,4-dinitrophenyl, digoxigenin, and biotin. Other suitable labeling reagents and preferred methods of attachment would be recognized by those of ordinary skill in the art of PNA, peptide or nucleic acid synthesis.

Fluorescent labels attached to the probes used with this invention are generally available as amine reactive labeling reagents. Preferred labeling reagents will be supplied as carboxylic acids or as the N-hydroxysuccinidyl esters of carboxylic acids. Preferred fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.). The most preferred fluorophores are the derivatives of fluorescein and particularly 5 and 6-carboxyfluorescein.

More preferably, the label attached to the probes of this invention are enzymes. Preferred enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Detectable and Independently Detectable Moieties/Multiplex Analysis:

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label two or more different probes used in an assay. The ability to differentiate between and/or quantitate each of the independently detectable moieties provides the means to multiplex a hybridization assay because the data that correlates with the hybridization of each of the distinctly (independently) labeled probe to a particular nucleic acid sequence can be correlated with the presence, absence or quantity of each organism sought to be detected in the sample. Consequently, the multiplex assays of this invention may be used to simultaneously detect the presence, absence or quantity of two or more organisms in the same sample and in the same assay. As used herein, the multiplex assay may be used to detect two or more yeasts of interest or at least one yeast and at least one other organism (e.g. bacteria), cell or tissue of interest.

Spacer/Linker Moieties:

Generally, spacers are used to minimize the adverse effects that bulky labeling reagents might have on hybridization properties of probes. Linkers typically induce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255–7258 (1998)). Preferably, a spacer/linker moiety comprises one or more linked compounds having the formula: $-Y-(O_m-(CW_2)_n)_o-Z-$. The group Y is selected from the group consisting of: a single bond, $-(CW_2)_p-C(O)(CW_2)_p-$, $-C(S)(CW_2)_p-$ and $-S(O_2)(CW_2)_p$. The group Z has the formula NH, $NR^2$, S or O. Each W is independently H, $R^2$, $-OR^2$, F, Cl, Br or I; wherein, each $R^2$ is independently selected from the group consisting of: $-CX_3$, $-CX_2CX_3$, $-CX_2CX_2CX_3$, $-CX_2CX(CX_3)_2$, and $-C(CX_3)_3$. Each X is independently H, F, Cl, Br or I. Each m is independently 0 or 1. Each n, o and p are independently integers from 0 to 10.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods and compositions described herein. Suitable in-situ hybridization conditions comprise conditions suitable for performing an in-situ hybridization procedure. Thus, suitable in-situ hybridization conditions will become apparent using the disclosure provided herein; with or without additional routine experimentation.

Blocking Probes:

Blocking probes are nucleic acid or non-nucleic acid probes that can be used to suppress the binding of the probing nucleobase sequence of the probing polymer to a non-target sequence. Preferred blocking probes are PNA probes (See: Coull et al., *WIPO publication No. WO98/24933*). Typically blocking probes are closely related to the probing nucleobase sequence and preferably they comprise one or more single point mutations of the probing segment. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the nucleic acid or non-nucleic acid probe to a non-target sequence.

Probing Nucleobase Sequence:

The probing nucleobase sequence of a probe is the specific sequence recognition portion of the construct. Therefore, the probing nucleobase sequence is a nucleobase sequence designed to hybridize to a target sequence within a yeast sought to be detected wherein the presence or absence of target sequence is used to detect the presence, absence or number of yeast of interest in the sample. Consequently, with due consideration of the requirements of a probe for the assay format chosen, the length of the probing nucleobase sequence will generally be chosen such that a stable complex is formed with the target sequence under suitable hybridization conditions or suitable in-situ hybridization conditions. Detection of the probe/target sequence hybrid can then be correlated with the presence, absence or number of yeast in the sample.

For the specific detection of *Dekkera/Brettanomyces* yeast and particularly *Dekkera bruxellensis* (*Brettanomyces*), the probing nucleobase sequence suitable for the practice of this invention, will generally, but not necessarily, have a length of 20 or fewer PNA subunits wherein at least a portion of the nucleobase sequence is at least 90% homologous to the probing nucleobase sequences listed in Table 1. Non-nucleic acid probes containing the shorter probing nucleobase sequences will typically be designed by truncating the probing nucleobase sequences listed in Table 1. However, the most preferred probing nucleobase sequences are listed in Table 1 and are preferably composed of PNA subunits. These probing nucleobase sequences have been shown to be specific for *Dekkera/Brettanomyces* yeast and particularly useful for the identification or quantitation of *Dekkera bruxellensis* (*Brettanomyces*). The most preferred probing nucleobase sequence for detecting wine spoilage organisms is Sequence ID No. 5 (BRE14).

A probe will preferably have a probing nucleobase sequence that is exactly complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15:331–335 (1997) and Guo et al., WO97/46711).

This invention further contemplates that variations in the probing nucleobase sequences listed in Table 1 shall provide probes which are suitable for the specific detection, identification or quantitation of *Dekkera/Brettanomyces* yeast and particularly *Dekkera bruxellensis* (*Brettanomyces*). Common variations include, truncations, deletions, insertions and frame shifts. Variation of the probing nucleobase sequences within the parameters described herein are considered to be an embodiment of this invention.

Probe Complexes:

In still another embodiment, two probes are designed to hybridize to the target sequence sought to be detected to thereby generate a detectable signal whereby the probing nucleobase sequence of each probe comprises half or approximately half of the complete target sequence of the yeast sought to be detected in the assay. As a non-limiting example, the probing nucleobase sequences of the two probes might be designed using the assay as described in European Patent Application 849,363, entitled "Method of identifying a nucleic acid using triple helix formation of adjacently annealed probes" by H. Orum et al. (*See: EPA* 849,363). Using this methodology, the probes that hybridize to the target sequence may or may not be labeled. However, it is the probe complex formed by the annealing of the adjacent probes that is detected. Similar compositions comprised solely of PNA probes have been described in copending and commonly owned application U.S. Ser. No. 09/302,238, herein incorporated by reference.

II. Preferred Embodiments of the Invention:

General Probes:

In one embodiment, this invention is directed to an enzyme-linked probe suitable for use in an in-situ hybridization assay and further characterized in that it comprises a probing nucleobase sequence directed to a target sequence within a yeast. By "enzyme-linked" we mean a nucleic acid or non-nucleic acid probe to which is covalently linked an enzyme. Non-limiting, exemplary enzymes suitable as detectable labels have been described herein (See: section entitled "Labels"). The probe may comprise a nucleic acid or non-nucleic acid probing nucleobase sequence but preferably the probing nucleobase sequence is of the non-nucleic acid type. Most preferably the probe is a PNA oligomer. The nucleobase sequence of the enzyme-linked probe is designed to detect specific yeasts, genius of yeasts or even be designed for the universal detection of all yeasts. An exemplary probing nucleobase sequence of a universal yeast probe would comprise a segment, at least a portion of which is, at least ninety percent homologous to the sequence: ACC-AGA-CTT-GCC-CTC-C (See: co-owned and copending U.S. Ser. No. 09/368,089, herein incorporated by reference) or the complement thereto.

The probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the probe is to be used. *Dekkera/Brettanomyces* Probes:

TABLE 1

| Sequence Name | rRNA Target | Probing Nucleobase Sequence | Sequence ID No. |
|---|---|---|---|
| BRE04 | 18S | AGC-GGG-TCT-ATT-AGA | Seq. ID No. 1 |
| BRE05 | 18S | CCA-GGT-GAG-GGT-CGC | Seq. ID No. 2 |
| BRE12 | 26S | CGG-TTG-CCC-GAT-TTC | Seq. ID No. 3 |
| BRE13 | 26S | TCG-CCT-TCC-TCC-TCT | Seq. ID No. 4 |
| BRE14 | 26S | CGG-TCT-CCA-GCG-ATT | Seq. ID No. 5 |
| BRE16 | 26S | CAC-AAG-ATG-TCC-GCG | Seq. ID No. 6 |
| BRE17 | 26S | GCG-GGC-ACT-AAT-TGA | Seq. ID No. 7 |
| BRE18 | 26S | CAT-CCA-CGA-GGA-ACG | Seq. ID No. 8 |
| BRE19 | 26S | GTG-TAA-ACC-AGG-TGC | Seq. ID No. 9 |
| BRE20 | 26S | ATG-GCT-CCC-AGA-ACC | Seq. ID No. 10 |
| BRE21 | 26S | GAC-AGA-ATC-GAA-GGG | Seq. ID No. 11 |

In another embodiment, this invention is directed to probes suitable for detecting, identifying or quantitating *Dekkera/Brettanomyces* yeast and particularly *Dekkera bruxellensis* (*Brettanomyces*) in a sample of interest. General characteristics (e.g. labels, spacers, linkers, probing nucleobase sequence length . . . etc.) of probes suitable for use in this invention have been previously described herein (See: section entitled "General"). The preferred probing nucleobase sequences of *Dekkera/Brettanomyces* yeast specific probes are listed in Table 1. Since the targets to these probes can be amplified by copying the target sequence, probes complementary to the sequences listed in the table (e.g. a copy of the target sequence) may also be used to detect *Dekkera/Brettanomyces* yeast and particularly *Dekkera bruxellensis*. The preferred probes for specifically detecting *Dekkera bruxellensis* are probes BRE12, BRE13, BRE14 and BRE16 with BRE14 being the most preferred. Preferably, but not necessarily, the *Dekkera/Brettanomyces* yeast specific probes of this invention are enzyme-linked and most preferably the enzyme is soy bean peroxidase.

In preferred embodiments, the probes of this invention are used in in-situ hybridization (ISH) and fluorescence in-situ hybridization (FISH) assays. Excess probe used in an ISH or FISH assay typically must be removed so that the detectable moiety of specifically bound probes can be detected above the background signal that results from still present but unhybridized probe. Generally the excess probe is washed away after the sample has been incubated with probe for a period of time. However, use of dark probes are a preferred embodiment of this invention, since there is no requirement that excess dark probe be completely removed (washed away) from the sample since it generates little or no detectable background.

As used herein, a "dark probe" means a nucleic acid or non-nucleic acid probe that hybridizes to a nucleic acid target to thereby cause a detectable change in at least one physical property of at least one attached label in a manner that can be used to detect, identify or quantitate the presence of an organism of interest in a sample of interest. Preferably, the organism is a yeast, though dark probes can be incorporated into sets of probes used for analysis of non-yeasts in combination with the analysis of yeast. Non-limiting examples of dark probes include PNA Molecular Beacons (See: WO99/21881 and U.S. Ser. No. 08/958,532 (abandoned) and copending and commonly owned U.S. Ser. No. 09/179,298, both incorporated herein by reference) as well as Linear Beacons (See: WO99/22018 and copending and commonly owned U.S. Ser. No. 09/179,162, herein incorporated by reference). Thus, changes in signal in the assay utilizing a "dark probe" can be directly correlated with hybridization of the probing nucleobase sequence to the target sequence of a yeast of interest.

Probe Sets:

In another embodiment, this invention is directed to a probe set suitable for detecting, identifying or quantitating *Dekkera/Brettanomyces* yeast in a sample and particularly *Dekkera bruxellensis* (*Brettanomyces*). The general characteristics of probes suitable for the detection, identification or quantitation of *Dekkera/Brettanomyces* yeast have been previously described herein with the preferred probing nucleobase sequences listed in Table 1.

The grouping of probes within sets characterized for specific detection of *Dekkera/Brettanomyces* yeast, and particularly *Dekkera bruxellensis* (*Brettanomyces*), is contemplated as a preferred embodiment of this invention. In one embodiment, the probes are grouped into a set to increase the signal in the assay by targeting a organism with several probes. In another embodiment, the grouping of probes within sets characterized for specific detection of both *Dekkera/Brettanomyces* yeast as well as other organisms of interest in the same sample and in the same assay is contemplated as still another preferred embodiment of this invention. The probes for the different organisms of interest are preferably independently detectable and thus suitable for multiplex analysis. In preferred embodiments, some of the probes of the set are blocking probes composed of PNA or nucleic acid.

The probes used for the detection of *Dekkera/Brettanomyces* yeast, and particularly *Dekkera bruxellensis* (*Brettanomyces*), can be organized into a set to improve sensitivity of the assay. Achieving high sensitivity is essential to rapid performance of the assay since the yeast are typically slow to grow (e.g. multiply to a detectable number). Thus, this invention is also directed to both a set of probes for the general detection of *Dekkera/Brettanomyces* yeast as well as a set of probes specific for the particularly detection of *Dekkera bruxellensis* (*Brettanomyces*).

Table 1 lists eleven probing nucleobase sequences suitable for the detection of *Dekkera/Brettanomyces* yeast. Consequently, one exemplary probe set would contain at least two probes suitable for detecting *Dekkera/Brettanomyces* yeast wherein said probes have a probing nucleobase sequence wherein at least a portion is at least ninety percent homologous to the sequences selected from the group consisting of: AGC-GGG-TCT-ATT-AGA (Seq. ID No. 1); CCA-GGT-GAG-GGT-CGC (Seq. ID No. 2); CGG-TTG-CCC-GAT-TTC (Seq. ID No. 3); TCG-CCT-TCC-TCC-TCT (Seq. ID No. 4); CGG-TCT-CCA-GCG-ATT (Seq. ID No. 5); CAC-AAG-ATG-TCC-GCG (Seq. ID No. 6); GCG-GGC-ACT-AAT-TGA (Seq. ID No. 7); CAT-CCA-CGA-GGA-ACG (Seq. ID No. 8); GTG-TAA-ACC-AGG-TGC (Seq. ID No. 9); ATG-GCT-CCC-AGA-ACC (Seq. ID No. 10) and GAC-AGA-ATC-GAA-GGG (Seq. ID No. 11) as well as sequences complementary thereto. The most preferred probing nucleobase sequences are exactly as represented above. In a preferred embodiment, the set contains probes comprising all of the above identified probing nucleobase sequences.

Another exemplary probes set would contain at least two probes suitable for detecting *Dekkera bruxellensis* yeast wherein said probes have a probing nucleobase sequence and wherein at least a portion is at least ninety percent homologous to the sequences selected from the group consisting of: CGG-TTG-CCC-GAT-TTC (Seq. ID No. 3); TCG-CCT-TCC-TCC-TCT (Seq. ID No. 4); CGG-TCT-CCA-GCG-ATT (Seq. ID No. 5) and CAC-AAG-ATG-TCC-GCG (Seq. ID No. 6). The most preferred probing nucleobase sequences are exactly as represented above. In a preferred embodiment, the set contains probes comprising all of the above identified probing nucleobase sequences.

Immobilization of Probes to a Surface:

One or more of the probes of this invention may optionally be immobilized to a surface for the detection of the target sequence. Generally, surface immobilized probes can be used in a capture assay. Probes can be immobilized to the surface using the well known process of UV-crosslinking. More preferably, the probe is synthesized on the surface in a manner suitable for deprotection but not cleavage from the synthesis support (See: Weiler, J. et al, Hybridization based DNA screening on peptide nucleic acid (PNA) oligomer arrays., Nucl. Acids Res., 25:2792–2799 (July, 1997)). In still another embodiment, one or more probes are covalently linked to a surface by the reaction of a suitable functional group on the probe with a functional group of the surface (See: Lester, A. et al, "PNA Array Technology": Presented at Biochip Technologies Conference in Annapolis (October, 1997)). This method is most preferred since the probes on the surface will typically be highly purified and attached using a defined chemistry, thereby minimizing or eliminating non-specific interactions.

Methods for the chemical attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the probe. Because native PNA possesses an amino terminus, a PNA will not necessarily require modification to thereby immobilize it to a surface (See: Lester et al., Poster entitled "PNA Array Technology").

Conditions suitable for the immobilization of a probe to a surface will generally be similar to those conditions suitable for the labeling of the polymer. The immobilization reaction is essentially the equivalent of labeling whereby the label is substituted with the surface to which the polymer is to be linked.

Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

Arrays of Probes or Probe Sets:

Arrays are surfaces to which two or more probes have been immobilized each at a specified position. Typically, the probing nucleobase sequence of the immobilized probes is judiciously chosen to interrogate (often using a capture or sandwich hybridization assay) a sample that may contain one or more organisms of interest. Because the location and composition of each immobilized probe is known, arrays are generally useful for the simultaneously detection, identification or quantitation of two or more organisms that may be present in the sample. Thus, arrays of probes or probe sets may be useful for repetitive screening of samples for yeast and particularly *Dekkera/Brettanomyces* yeast. The arrays of this invention comprise at least one probe (as described herein) suitable for the detection, identification or quantitation of yeast and particularly *Dekkera/Brettanomyces* yeast. The general characteristics of probes suitable for the detection, identification or quantitation of *Dekkera/Brettanomyces* yeast, and particularly *Dekkera bruxellensis* (*Brettanomyces*) have been previously described herein. Preferred probing nucleobase sequences for the immobilized probes are listed in Table 1.

General Method:

In yet another embodiment, this invention is generally directed to a method for the detection, identification or quantitation of yeast using enzyme-linked probes (nucleic acid or non-nucleic acid) in an in-situ hybridization (ISH) assay. According to the method, a sample containing one or more species of yeast is contacted with a yeast specific enzyme-linked probe, under suitable in-situ hybridization conditions. The enzyme-linked probe will hybridize to the target sequence of the yeast, if present in the in-situ assay, and the activity of the enzyme can be used to detect, identify or quantitate the yeast present in the sample. In a preferred embodiment, the target sequence is a rRNA sequence. Non-limiting exemplary enzymes suitable as detectable labels are previously described in the section entitled "Labels". The probe may comprise a nucleic acid or non-nucleic acid probing nucleobase sequence but preferably the probing nucleobase sequence is of the non-nucleic acid type and most preferably the probe is a PNA. The nucleobase sequence of the enzyme-linked probe can be designed to detect specific yeasts, genius of yeasts or even be designed for the universal for the detection of all yeasts.

*Dekkera/Brettanomyces* Specific Methods:

In another embodiment, this invention is directed to a method suitable for detecting, identifying or quantitating *Dekkera/Brettanomyces* yeast, and particularly *Dekkera bruxellensis* (*Brettanomyces*) in a sample. The general characteristics of probes suitable for the detection, identification or quantitation of *Dekkera/Brettanomyces* yeast, and particularly *Dekkera bruxellensis* (*Brettanomyces*) have been previously described herein. Preferred probing nucleobase sequences are listed in Table 1.

The method for detecting, identifying or quantitating *Dekkera/Brettanomyces* yeast in a sample comprises contacting the sample with one or more *Dekkera/Brettanomyces* yeast specific probes to thereby form, under suitable hybridization conditions, a probe/target sequence hybrid that can be detected. Preferably, the one or more probes comprises a probing nucleobase sequence wherein at least a portion is at least ninety percent homologous to the sequences selected from the group consisting of: AGC-GGG-TCT-ATT-AGA (Seq. ID No. 1); CCA-GGT-GAG-GGT-CGC (Seq. ID No. 2); CGG-TTG-CCC-GAT-TTC (Seq. ID No. 3); TCG-CCT-TCC-TCC-TCT (Seq. ID No. 4); CGG-TCT-CCA-GCG-ATT (Seq. ID No. 5); CAC-AAG-ATG-TCC-GCG (Seq. ID No. 6); GCG-GGC-ACT-AAT-TGA (Seq. ID No. 7); CAT-CCA-CGA-GGA-ACG (Seq. ID No. 8); GTG-TAA-ACC-AGG-TGC (Seq. ID No. 9); ATG-GCT-CCC-AGA-ACC (Seq. ID No. 10) and GAC-AGA-ATC-GAA-GGG (Seq. ID No. 11), and complements thereto. The most preferred probing nucleobase sequences are exactly as represented above.

According to the method *Dekkera/Brettanomyces* yeast, and particularly *Dekkera bruxellensis* (*Brettanomyces*) in the sample, are then detected, identified or quantitated. Detection, identification and/or quantitation of *Dekkera/Brettanomyces* yeast is made possible by correlating the presence of the probe/target sequence hybrid with the presence, absence or number of *Dekkera/Brettanomyces* yeast in the sample. The method is preferably, but not necessarily performed as an in-situ hybridization assay.

The grouping of probes within probe sets to be used in the methods for detecting *Dekkera/Brettanomyces* yeast as well as other organisms in the same sample and in the same assay (a multiplex assay) is contemplated as a preferred embodiment of this invention. In a preferred embodiment, probes used in the methods to detect *Dekkera/Brettanomyces* yeast and other organisms are each labeled with independently detectable fluorophores to thereby enable correlation of the presence of signal from a particular fluorophore with the presence of one of either *Dekkera/Brettanomyces* yeast or another organism of interest. Exemplary probe sets suitable for the practice of this multiplex method have been previously described herein.

Unlabeled Non-Nucleic Acid Probes

The probes of this invention need not be labeled with a detectable moiety to be operable within the method of this invention. When using the probes of this invention it is possible to detect the probe/target sequence complex formed by hybridization of the probing nucleobase sequence of the probe to the target sequence. For example, a PNA/nucleic acid complex formed by the hybridization of a PNA probing nucleobase sequence to the target sequence could be detected using an antibody that specifically interacts with the complex under antibody binding conditions. Suitable antibodies to PNA/nucleic acid complexes and methods for preparation and use are described in WIPO Patent Application WO95/17430 and U.S. Pat. No. 5,612,458, herein incorporated by reference.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety such as an enzyme. Suitable detectable moieties have been previously described herein. Thus, the presence, absence or quantity of the detectable moiety is correlated with the presence, absence or quantity of the antibody/PNA/nucleic acid complex and the organism to be identified by the probing nucleobase sequence of the PNA probe. Alternatively, the antibody/PNA/nucleic acid complex is detected using a secondary antibody that is labeled with a detectable moiety. Typically the secondary antibody specifically binds to the α-PNA/nucleic acid antibody under antibody binding conditions. Thus, the presence, absence or quantity of the detectable moiety is correlated with the presence, absence or quantity of the antibody/antibody/PNA/nucleic acid complex and the organism to be identified by the probing nucleobase sequence of the probe. As used herein, the term antibody shall include antibody fragments that specifically bind to other antibodies or other antibody fragments.

Exemplary Assay Formats:

Yeast that have been treated with the probes, probe sets or kits of this invention can be detected by several exemplary methods. The yeasts can be fixed on slides, or preferably on membranes or other filtration media, and then visualized with a microscope, CCD camera or film (See for example: Examples 10–13).

Methods used to experimentally test specific PNA probes in PNA-ISH assays can be found in Example 10 of this specification. Demonstrations of PNA-FISH are presented in Example 14. As a whole, the examples contained in this specification demonstrate that both enzyme-linked and fluorescently labeled probes comprising the probing nucleobase sequences listed in Table 1 are specific for detecting *Dekkera/Brettanomyces* yeast. Using the SBP-linked probe, the experimental conditions presented in the Examples yield results within 1–2 days with the lions share of the time allocated to growth of the yeast. Whether SBP or fluorescently labeled probes are used, the non-growth portion of the *Dekkera/Brettanomyces* yeast assay is performed in less than 3 hours with the PNA probe hybridization typically requiring as little as 30 minutes. Generally this assay format was found to be sensitive and reliable without regard to the nature of the target sequence.

Exemplary Media Based Analysis Of Slow Growing Yeasts

The methods, kits and compositions of this invention are particularly useful for the rapid probe-based detection, identification and quantitation of slow growing yeasts such as *Dekkera/Brettanomyces*; particularly in the analysis of wine. For example, Applicants have demonstrated (See: Example 10 of this specification) the use of enzyme-linked yeast specific PNA probes in combination with in-situ analysis of microcolonies of yeast grown (using selective media) directly on the medium on which they were isolated from the sample (i.e. a filtration membrane) to thereby achieve the rapid, sensitive and specific analysis of *Dekkera/Brettanomyces* yeast that was not previously possible.

The rapid probe-based analysis of slow growing yeasts, such as *Dekkera/Brettanomyces* yeast, requires very high sensitivity in addition to probe specificity because the cell count is limited. Probe-based analysis of slow growing yeast was chosen as the format so that the yeasts could be positively identified and distinguished from non-spoilage yeasts. Since probe-based analysis detects nucleic acid, the analysis of cells in culture is used to distinguish between viable organisms and dead (non-viable) organisms, the presence of which are not necessarily considered to cause food or beverage spoilage or contamination.

Enzyme-linked probes were chosen since the enzymes can rapidly and repetitively turn over a substrate to thereby achieve signal amplification suitable for high sensitivity detection. Preferred, non-limiting, substrates include chemiluminescent compounds, fluorophores and chromophores. PNA probes were chosen, as the preferred probe type, since they hybridize rapidly to nucleic acid, are generally more specific than nucleic acid probes, operate under conditions of low ionic strength (favored conditions for hybridizing to structured rRNA) and form very stable hybrids. In-situ analysis of cultured yeast was chosen since viability of colony forming units (CFU) could be absolutely determined and optionally quantitated by scoring the colonies observed in the culture.

In preferred embodiments, the yeast culture is generated directly on an isolation medium that is integrated into the yeast culture. Integration of the isolation medium with the yeast culture, eliminates the need for a transfer pre- and post-culture growth and thereby eliminates the opportunity for error associated therewith. Preferably, the isolation medium is a filter or a membrane filter. Preferred filters are microporous membrane filters such as those sold by Millipore Corporation for the filtration of liquids. Pore sizes of the filter are generally chosen so that the yeasts will not pass though the pores thereby insuring that all the yeast in the sample is collected on the filter. With regard to the analysis of wine, the use of a microporous membrane filter as the isolation medium allows for the collection of yeasts by filtration of a known volume of wine.

Once the sample is collected on the isolation medium, a culture is grown in a manner specific for the organism or organisms of interest using methods known in the art. Preferably, the culture is grown using a selective culture media. By "selective culture media" we mean a culture media that will support the specific growth of the organism or organisms (e.g. yeast or yeasts) of interest while inhibiting the growth of non-target organisms that might cause non-specific signal in the assay. For example, Applicants are aware of certain organisms having endogenous peroxidase activity that will generate signal, in the presence of the chemiluminescent substrate used in the assay described in Example 10, in the absence of any enzyme-linked probe.

After the yeast culture is grown, typically the yeast will be fixed. Cell fixation is a term well known in the art of in-situ hybridization and is generally, but not necessarily, part of the in-situ hybridization process.

Using probe-based in-situ analysis of the isolation medium after culture, the number of colony forming units (CFU) of the yeast, which are detected by the yeast specific probe, can be counted or scored (manually or by automated methods) after an appropriate incubation period. Applicant's data indicates that 24 hours of incubation may be acceptable but very reliable results require approximately 40 hours of culture incubation. Thus, the assay can typically be completed in 27 to 48 hours. Because the yeast are preferably grown directly on the isolation medium, the colonies detected are each representative of a colony forming unit (CFU) isolated from the sample. Since the volume of liquid (e.g. wine) filtered to isolate the yeast is known and since only viable organisms grow, the CFU's per unit volume of liquid can be directly determined.

Kits:

In yet another embodiment, this invention is directed to kits suitable for performing an assay that detects the presence, absence or number of yeast in a sample. The invention is also more specifically directed to kits suitable for performing an assay that detects the presence, absence or number of *Dekkera/Brettanomyces* yeast, and particularly *Dekkera bruxellensis* (*Brettanomyces*) in a sample. For the kits directed to yeast, the kit must comprise an enzyme-linked probe and most preferably an enzyme-linked PNA probe. The general characteristics of probes suitable for the detection, identification or quantitation of *Dekkera/Brettanomyces* yeast have been previously described herein with the preferred probing nucleobase sequences listed in Table 1. Furthermore, methods suitable for using the nucleic acid probes, non-nucleic acid probes or probe sets of a kit to detect, identify or quantitate *Dekkera/Brettanomyces* yeast in a have been previously described herein.

The kits of this invention comprise one or more probes and other reagents or compositions that are selected to perform an assay or otherwise simplify the performance of an assay used to detect, identify or quantitate *Dekkera/Brettanomyces* yeast in a sample. In kits that contain sets of probes, wherein each of at least two probes of the set are used to distinctly detect and distinguish between *Dekkera/Brettanomyces* yeast and other organisms that might be present in a sample in the same assay, the probes of the set are preferably labeled with independently detectable moieties so that organisms of interest can be individually detected, identified or quantitated (a multiplex assay). In a preferred embodiment, probes of a kit that are used to detect *Dekkera/Brettanomyces* yeast and other organisms are labeled with independently detectable fluorophores to thereby enable correlation of the presence of signal from a particular fluorophore with the presence of one of either the yeast or other organism of interest in the sample.

Components of an exemplary kit suitable for detecting yeast in a sample might comprise some or all of the following: 1) a filter (e.g. a microporous membrane filter) for isolating yeast from a sample of interest; 2) culture media (preferably semi-exclusive) for growing the isolated yeast and/or bacteria; 3) a fixation solution for fixing culture grown yeast; 4) a hybridization solution suitable for imposing suitable hybridization conditions; 5) an enzyme-linked probe (preferably, a soy bean peroxidase labeled PNA probe) specific for detecting, identifying or quantitating the yeast and/or other organisms sought to be detected in the sample; 6) one or more wash solutions for removing undesirable components after performing one or more steps of the assay; 7) an enzyme substrate suitable for generating detectable signal from the enzyme activity of the enzyme-linked probe; and 8) a film for detecting signal generated from the enzyme activity. Preferably, the enzyme-linked probe is specific for the detection of *Dekkera/Brettanomyces* yeast and particularly *Dekkera bruxellensis* (*Brettanomyces*) in wine.

Exemplary Applications for Using the Invention:

Whether support bound or in solution, the probes, probe sets, methods and kits of this invention are particularly useful for the rapid, sensitive, reliable and versatile detection of yeast in food, pharmaceutical products, personal care products, dairy products as well as environmental and clinical samples. More preferably they are used in the analysis of beverages including soda, bottled water, fruit juice, beer or liquor products and most preferably Applicants have demonstrated the utility of the probes of this invention for the analysis of wine. Suitable probes, probe sets, methods and kits will be particularly useful for the analysis of raw materials, equipment, products or processes used to manufacture or store food, pharmaceutical products, personal care products, dairy products, environmental samples or beverages including soda, bottled water, fruit juice, beer or liquor products and most preferably wine. In particular, the probes, probe sets, methods and kits of this invention are particularly useful for the detection of *Dekkera/Brettanomyces* yeast or *Dekkera bruxellensis* (*Brettanomyces*) in wineries and breweries.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following examples that are not intended to be limiting in any way.

Example 1

Synthesis of bis-(2-methoxyethyl)amidyl-diglycolic acid

To 60 mmol of bis(2-methoxyethyl) amine (Aldrich Chemical), 65 mmol triethylamine and mL of dichloromethane (DCM) was added portionwise 50 mmol of diglycolic anhydride (Aldrich Chemical). The reaction was immediate and violent but was allowed to stir overnight. The reaction was worked up by evaporation to a brown oil. The residue was redissolved in 50 mL of DCM and then transferred to a separatory funnel. The DCM layer was extracted with 100 mL of 10% aqueous citric acid. The aqueous layer was then back extracted 5×25 mL of DCM. All DCM layers were combined and extracted 1× with 25 mL of 10% aqueous citric acid. The DCM layer was separated, dried ($Na_2SO_4$), filtered and evaporated to yield 6.6 g (26.5 mmol; 53% yield).

Large Scale:

To 500 mmol of diglycolic anhydride stirring in 800 mL of dichloromethane (DCM) was added dropwise, 1.1 mole of bis(2-methoxyethyl)amine (Aldrich Chemical). The reaction was allowed to stir for 2 hours and then 280 mL of 6N HCl was added dropwise. The contents were then transferred to a separatory funnel and allowed to separate. The DCM layer was removed and the aqueous layer extracted with 100 mL of DCM. The combined DCM layers were then extracted with 100 mL of 10% aqueous citric acid. The DCM layer was then separated, dried ($Na_2SO_4$), filtered and evaporated to yield 73.8 g (296 mmole; 59% yield). A kugelrorh was then used to remove traces of solvent (product was heated to 60° C. at approximately 180 µM Hg).

Example 2

Synthesis of N-[N"-Fmoc-(2"-aminoethyl)]-N-[N, N'-(2-methoxyethyl)amidyl-diglycolyl]glycine (Fmoc-"E"aeg-OH)

To 8 mmol of Fmoc-aeg-OH (PerSeptive Biosystems, Inc.) was added 24 mL of acetone and 40 mL of MilliQ water. To this stirring solution was added 16 mmol of $NaHCO_3$, and 8 mmol of $K_2CO_3$. This solution was allowed to stir until all the Fmoc-aeg-OH had dissolved (approx. 1 hr.) and then the solution prepared, as described below, was added.

To 9 mmol of bis-(2-methoxyethyl)amidyl-diglycolic acid was added 20 mL of anhydrous acetonitrile (Fluka Chemical), 27 mmol of N-methylmorpholine (NMM; Fluka Chemical) and 9.3 mmol of trimethylacetyl chloride (Aldrich Chemical). The solution was allowed to stir at room temperature for 30 minutes and then added dropwise to the solution of Fmoc-aeg-OH that was prepared as described above.

After the combined solutions stirred for 1 hr and tlc analysis indicated complete reaction, the organic solvents were removed by vacuum evaporation. The remaining aqueous solution was then acidified to pH 4.5 by the portionwise addition of citric acid. The solution was then transferred to a separatory funnel and extracted 4× with 35 mL of ethyl acetate. The combined ethyl acetate layers were then added to the separatory funnel. To the contents was added 4 mL of NMM and 35 mL of water. The contents of the separatory funnel were mixed and the aqueous layer collected after separation. The ethyl acetate layer was washed 1× with 10 mL of water. The water layers were combined and acidified to pH<3 by portionwise addition of citric acid. This aqueous solution was then extracted 3× with 35 mL of ethyl acetate with all ethyl acetate layers being combined, dried ($Na_2SO_4$), filtered and evaporated to yield 5.6 g white foam.

This crude product was, twice, dissolved in DCM and then precipitated into a mixture of 2/1 hexane/diethyl ether. The precipitation was performed twice to remove all traces of trimethylacetic (pivalic) acid. The final product was collected by vacuum filtration. Yield 2.67 g (4.7 mmol; 58%).

For larger scale syntheses, the precipitation procedure described above did not remove substantially all of the trimethylacetic (pivalic) acid. Thus, for larger scales crude product was purified by column chromatography using a reversed phase stationary phase (C18) and a gradient of aqueous acetonitrile to elute the product and remove the pivalic acid. Though not visible by tlc, the elution of the pivalic acid can be monitored by smell. The pivalic acid can be almost completely eluted from the column prior to elution of the product. Elution of the product can be monitored by tlc.

This "Fmoc-"E"aeg-OH" monomer was used directly on the PNA synthesis instrument, using standard condensation conditions, or used to prepare prederivatized synthesis supports that were used for the preparation of C-terminally "E" modified PNAs. An "E" modification (subunit) of a PNA or polyamide has the formula:

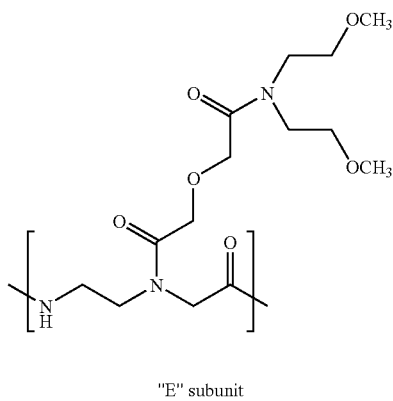

"E" subunit

Example 3

Synthesis of 4-(N-(tert-butyloxycarbonyl)-aminobenzoic Acid:

To 100 mM of methyl-4-amino benzoic acid stirring in 150 mL of dioxane was added 110 mM of di-tert-butyl-dicarbonate. The reaction was warmed to 70–80° C. and let stir for about 48 hours. The solvent was then evaporated under reduced pressure and the residue redissolved in about 300 mL of ethylacetate. The organic layer was then washed three times with 10% aqueous citric acid, dried ($Na_2SO_4$), filtered and evaporated to a solid. The solid was then suspended in 150 mL of 1N NaOH and 50 mL acetone. Saponification of the ester was allowed to run overnight until complete hydrolysis was observed by thin layer chromatography (TLC). To the solution was added citric acid until the pH of the solution was approximately 4. The solid was then collected by vacuum filtration and dried in a vacuum oven at 50° C. Yield 20.3 g, 85%. The product was a single peak when analyzed by reversed phase High Performance Liquid Chromatography (HPLC) using 0.1% aqueous trifluoroacetic acid (TFA) and a linear acetonitrile gradient.

Example 4

Synthesis of PNAs

Unless otherwise stated, PNAs were synthesized using commercially available reagents and instrumentation obtained from PerSeptive Biosystems, Inc., Framingham, Mass., USA. PNAs having modifications of "E" or "P" modifications ("P" is aminobenzoic acid) were prepared using the general methods, monomers and compositions described herein.

Example 5

Preferred Method For Removal Of The Fmoc Protecting Group

The synthesis support was treated with a solution of 25% piperidine in DMF for 10–15 minutes at room temperature. After treatment, the synthesis support was washed and dried under high vacuum. The support can the be treated with labeling reagent such as protected 4-aminobenzoic acid (See: Example 6).

Example 6

N-terminal Labeling of Arylamine Labeled Peptide Nucleic Acids:

Labeling of the amino terminus of the PNA oligomer with a linker group while the oligomer was still support bound was accomplished by condensation of two subunits of Expedite PNA Linker (P/N GEN063032) using one of the auxiliary positions of the PNA synthesizer and the standard coupling cycle. To the amino terminus (final Fmoc group removed) of the elongated polymer was condensed 4-(N-(tert-butyloxycarbonyl)-aminobenzoic acid (See: Example 3). Condensation of 4-(N-(tert-butyloxycarbonyl)-aminobenzoic acid with the N-terminus was typically performed manually using conditions similar to those used on the PNA synthesizer except that the concentration of reagents and reaction time was usually increased. After desired modification of the amino terminus of the polymer, the oligomers were then cleaved from the support, deprotected and purified using reversed phase HPLC.

Example 7

General Procedure For Labeling of Support Bound PNA with 5(6)carboxyfluorescein

After proper reaction with linkers and removal of the terminal amine (Fmoc) protecting group, the resin was treated with 250 µL of a solution containing 0.5M 5(6) carboxyfluorescein, 0.5M N,N'-diisopropylcarbodiimide, 0.5M 1-hydroxy-7-azabenzotriazole (HOAt) in DMF (See: Weber et al., *Bioorganic & Medicinal Chemistry Letters*, 8: 597–600 (1998). After treatment the synthesis support was washed and dried under high vacuum. The PNA oligomer was then cleaved, deprotected and purified as described below.

Fluorescein Labeled PNA Oligomers Prepared:

TABLE 2

| Probe ID | PNA Probe Sequence |
|---|---|
| Flu-BRE04 | Flu-OO-AGC-GGG-TCT-ATT-AGA-EE-$NH_2$ |
| Flu-BRE05 | Flu-OO-CCA-GGT-GAG-GGT-CGC-EE-$NH_2$ |
| Flu-BRE12 | Flu-OE-CGG-TTG-CCC-GAT-TTC-EE-$NH_2$ |
| Flu-BRE13 | Flu-OE-TCG-CCT-TCC-TCC-TCT-EE-$NH_2$ |
| Flu-BRE14 | Flu-OE-CGG-TCT-CCA-GCG-ATT-EE-$NH_2$ |
| Flu-BRE16 | Flu-OE-CAC-AAG-ATG-TCC-GCG-EE-$NH_2$ |

TABLE 2-continued

| Probe ID | PNA Probe Sequence |
|---|---|
| Flu-BRE17 | Flu-OE-GCG-GGC-ACT-AAT-TGA-EE-NH$_2$ |
| Flu-BRE18 | Flu-OO-CAT-CCA-CGA-GGA-ACG-EE-NH$_2$ |
| Flu-BRE19 | Flu-OE-GTG-TAA-ACC-AGG-TGC-EE-NH$_2$ |
| Flu-BRE20 | Flu-OE-ATG-GCT-CCC-AGA-ACC-EE-NH$_2$ |
| Flu-BRE21 | Flu-OE-GAC-AGA-ATC-GAA-GGG-EE-NH$_2$ |

Example 8

General Procedure for Cleavage, Deprotection and Purification

The synthesis support (Fmoc-PAL-PEG/PS; P/N GEN913384) was then removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) was then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using reversed phase chromatographic methods known in the art.

Note: Several PNAs were prepared using new product Fmoc-XAL-PEG/PS synthesis support (P/N GEN 913394) available from PerSeptive Biosystems Inc. This support has the advantage that the PNA can be removed more rapidly and under more mildly acid conditions. For PNAs prepared with Fmoc-XAL-PEG/PS the support is treated as described above except that a solution of TFA/m-cresol 9/1 was used for a period of 10–15 minutes (2×).

Example 9

General Procedure for Conjugation of Arylamine Containing Probes to Soy Bean Peroxidase Stock Solutions:

1. Probe Stock:

Purified arylamine terminated probe, typically fifteen residues in length, was dissolved at a concentration of approximately 0.33 µmol per milliliter in 50% aqueous dimethylformamide (DMF) for PNA or 20% aqueous acetonitrile for nucleic acid.

2. Enzyme Stock:

Soy bean peroxidase, conjugate grade, obtained from Wiley Organics, was dissolved at a concentration of 8.0 mg per milliliter in an aqueous buffer comprised of 0.3 M NaCl, 10 mM MgCl$_2$, 0.1 mM ZnCl$_2$ and 30 mM N-methylmorpholine adjusted to pH 7.6 with 12 N hydrochloric acid.

3. 30% Aqueous DMF:

An aqueous DMF solution was prepared by combining three volumes of DMF with 7 volumes of water.

4. MES Buffer

An 0.2 M solution of 4-morpholineethanesulfonic acid (MES) in water was prepared (not pH adjusted).

5. Glycine Solution

A solution comprised of 0.5 M glycine and 0.25 M sodium hydroxide in water was prepared.

6. Wash Buffer

An aqueous buffer comprised of 0.15 M NaCl, 5 mM MgCl$_2$, 0.05 mM ZnCl$_2$ and 15 mM N-methylmorpholine adjusted to pH 7.6 with hydrochloric acid was prepared.

7. Storage Buffer

An aqueous buffer comprised of 0.3 M NaCl, 10 mM MgCl$_2$, 0.1 mM ZnCl$_2$ and 30 mM N-methylmorpholine adjusted to pH 7.6 with 12 N hydrochloric acid was prepared.

8. Stabilization Buffer

Peroxidase Stabilizing Buffer, DAKO Diagnostics Canada Inc.; Part No. D210084

TABLE 3

| Probe ID | PNA Probe Sequence |
|---|---|
| SBP-BRE04 | SBP-POO-AGC-GGG-TCT-ATT-AGA-EE-NH$_2$ |
| SBP-BRE05 | SBP-POO-CCA-GGT-GAG-GGT-CGC-EE-NH$_2$ |
| SBP-BRE12 | SBP-POO-CGG-TTG-CCC-GAT-TTC-EE-NH$_2$ |
| SBP-BRE13 | SBP-POO-TCG-CCT-TCC-TCC-TCT-EE-NH$_2$ |
| SBP-BRE14 | SBP-POO-CGG-TCT-CCA-GCG-ATT-EE-NH$_2$ |
| SBP-BRE16 | SBP-POO-CAC-AAG-ATG-TCC-GCG-EE-NH$_2$ |
| SBP-BRE17 | SBP-POO-GCG-GGC-ACT-AAT-TGA-EE-NH$_2$ |
| SBP-BRE18 | SBP-POO-CAT-CCA-CGA-GGA-ACG-EE-NH$_2$ |
| SBP-BRE19 | SBP-POO-GTG-TAA-ACC-AGG-TGC-EE-NH$_2$ |
| SBP-BRE20 | SBP-POO-ATG-GCT-CCC-AGA-ACC-EE-NH$_2$ |
| SBP-BRE21 | SBP-POO-GAC-AGA-ATC-GAA-GGG-EE-NH$_2$ |
| SBP-Zba03 | SBP-POO-CGA-GCG-AAA-CGC-CTG-EE-NH$_2$ |
| SBP-EuUni01 | SBP-POO-ACC-AGA-CTT-GCC-CTC-E-NH$_2$ |
| SBP-BacUni01 | SBP-POO-CTG-CCT-CCC-GTA-GGA-EE-NH$_2$ |

All PNA sequences are written from the amine (N-) terminus to the carboxyl (C—) terminus. SBP=soy bean peroxidase; P=4-aminobenzoic acid; E is defined above; and O=8 amino-3.6-dioxaoctanoic acid.

Exemplary Small Scale Conjugation Procedure:

Note: This procedure has been successfully scaled at least 10 fold.

In a reaction tube was combined 20 µL of Enzyme Stock, 12.5 µL of 30% Aqueous DMF, and 7 µL of Probe Stock. In a separate tube was placed 1 mg of 1-(3-dimethylaminopropyl)-3-ethylcarbodiimide hydrochloride (EDC) and 10 µL of MES Buffer. These reagents were mixed, just prior to addition to the reaction, until the EDC had dissolved in the MES Buffer. The EDC/MES Buffer solution was then added to the tube containing the enzyme and probe (Reaction Mixture). The contents were mixed, and the tube was placed at 0° C. for 40 min. To the Reaction Mixture was then added 7 µL of Glycine Solution. The contents were again mixed and the tube was placed at 0° C. for a further 20 minutes.

Exemplary Conjugate Purification Procedures:

We have used both ultrafiltration and gel filtration chromatography for the purification of the enzyme-linked probe from excess enzyme and excess probe. At this time we prefer to use gel filtration chromatography though these as well as other methods of separation may work equally well. Exemplary methods for both purification procedures will be described below.

Ultrafiltration

As an example of ultrafiltration, the contents of the tube (See: Exemplary Small Scale Conjugation Procedure) were diluted with 50 μL of Wash Buffer and then transferred to the cup of an ultrafiltration device (e.g. 30,000 molecular weight cut-off, Millipore Corporation, Bedford Mass.) and spun at 5,000×g until ~90% of the liquid had been removed from the cup. An additional 50 μL of Wash Buffer was then be added to the cup and the device spun again to remove 90% of the liquid. This washing procedure was preferably repeated two additional times. The contents of the cup were then diluted to a volume of 1 milliliter in Storage Buffer. The absorbance of this solution (at 260 nm) was then used to estimate the concentration of the enzyme conjugate (0.05 absorbance units at 260 nanometers per milliliter is typically estimated to be 0.33 nmol per milliliter based on an estimated extinction for a PNA 15-mer of 150 optical density units per μmole of probe).

Gel Filtration Chromatography

At this time however, we prefer to separate the crude reaction mixture using gel filtration chromoatography (e.g. Superdex 200 (Part No. 17-1043-01) from Amersham Pharmacia or a BioRad prepacked gel filtration BioSelect SEC 250-5 column (Part No. 125-0476)). The mobile phase was aqueous 0.1M NaCl and 0.1M bis-tris HCl (Research Organics; Part No. 1164B) pH 6.5 with 10% acetonitrile. After Gel Filtration Chromatography, the fractions were desalted and resuspended in Stabilization Buffer (this buffer is superior to the Storage Buffer for long term storage of the conjugate). Desalting was performed by loading the fractions on a preconditioned (See: Manufacturers instructions) Oasis™ prepackaged column (Waters; Part No. 094225 (30 mg); 094226 (60 mg) or 106202 (200 mg)). Once loaded, the enzyme conjugate was eluted from the stationary phase using a solution containing 0.01 M NaCl, 0.02 M Tris pH 7.4 with a stepwise (10% per step) gradient of aqueous acetonitrile (usually requiring 30% aqueous acetonitrile to elute the product). The absorbance of this solution (at 260 nm) was then used to estimate the concentration of the enzyme conjugate (0.05 absorbance units at 260 nanometers per milliliter is typically estimated to be 0.33 nmol per milliliter based on an estimated extinction for a PNA 15-mer of 150 optical density units per μmole of probe). The aqueous acetonitrile was removed by vacuum evaporation and the conjugate resuspended in Stabilization Buffer based on the pre-evaporation quantity of conjugate in the sample. Generally, the conjugate was resuspended to a concentration of 10 μM in Stabilization Buffer and stored at −20° C. The SBP labeled probes can optionally be diluted to 100 nM in Stabilization Buffer and stored at 4° C.

Final Probe Preparation

Regardless of which purification method is used, the products are typically screened using dot blot analysis in nylon membrane (See Example 10) to determine sensitivity, specificity and noise. Analysis was performed after the fractions were transferred to Storage Buffer or Stabilization Buffer.

Example 10

Analysis of *Dekkera/Brettanomyces* Yeast:

I. Dot Blot Analysis of Fluorescein (as a Hapten) Labeled PNA Probes rRNA Preparation:

Using a Qiagen kit (P/N 75144), total RNA (including app. 80% rRNA) was isolated from the different yeast species that had been grown in culture. The amount of RNA isolated was determined by measuring the absorption at 260 nm.

Hybridization to the Membranes:

Dot blots were made on nylon membranes obtained from Gibco-BRL (P/N 14830-012). For the RNA of each cultured yeast, a dilution row containing 5 spots was made, starting with a concentration of 16 ng/μL RNA for the strongest solution and continuing with half log dilutions in diethyl pyrocarbonate (DEPC) treated water (RNase free). Prior to spotting on the membrane, each dilution stock was heated to 68° C. for three minutes. The spotting produced a half log dilution series containing approximately 16, 5.1, 1.6, 0.52, and 0.17 ng total RNA per spot. Once the spots had air dried, the membrane was UV-cross-linked and then stored in a plastic bag until used.

Individual membranes were placed in plastic bags and pre-wet with RNase-free water. The membranes were pre-hybridized in Hybridization Buffer 1 (20 mM Tris-HCl, pH 7.5; 50% formamide; 0.1% sodium dodecyl sulphate (SDS); and 100 mM NaCl) for 15 minutes at 50° C.

All probes were diluted in 1:1 DMF/H$_2$O to a concentration of approximately 300 pmole/μL and then diluted to a final concentration of 5 pmol/mL each using Hybridization Buffer 1. The hybridization buffer was then removed from the bags and fresh Hybridization Buffer 1 containing one of the probes listed in Table 2 was added to each of the bags (all probes were tested individually).

The hybridization was performed at 50° C. for 1 hour. The filters were then washed 3 times in TE-7.5 (10 mM Tris-HCl, pH 7.5, 1 mM EDTA) containing 0.2% SDS. The first wash was at room temperature for 5 minutes. The second and third washes were at 60° C. for 10–15 minutes each.

Visualization of the Membrane:

After the washes were completed, the membranes were treated with a blocking solution (50 mM Tris-HCl, pH 9.0; 0.5 M NaCl; and 0.5% casein). The starting temperature of the solution was 65° C., but the solution cooled as the blocking proceeded with shaking at room temperature for 15 minutes. An anti-fluorescein-alkaline phosphatase conjugate (Rabbit (Fab) anti-FITC/AP (DAKO A/S, P/N K0046)) was diluted 1:1000 in blocking solution and the membranes were left shaking in this solution for 30 minutes at room temperature. The membranes were then washed in 50 mM Tris-HCl, pH 9.0; 0.5 M NaCl; and 0.5% Tween-20 three times each for 5 minutes. To prepare the membranes for the detection, a final rinse was performed with 10 mM Tris-HCl, pH 9.5; 10 mM NaCl; and 1 mM MgCl$_2$. The chemiluminescent substrate (AMPPD, Tropix Corp., P/N PD025) was diluted 1:100 in an aqueous substrate (0.1 M diethanolamine, pH 9.7; and 1 mM MgCl$_2$) and the membranes were immersed for 4 minutes. The membranes were placed in a plastic bag and excess substrate was squeezed out and the bag sealed. The membranes were exposed to Fuji-RX X-ray film for between 5 and 30 minutes.

With reference to Table 4, total-RNA of each of the following yeast species was spotted on membranes: *Dekkera anomala*, NRRL #Y-17522; *Dekkera bruxellensis*, NRRL #Y17527; *Brettanomyces custersianus*, NRRL #Y-6653; *Brettanomyces naardenensis*, NRRL #Y17527; and *Brettanomyces nanus*, NRRL #Y-1614. The specificity of the PNA probes was examined. PNA probes BRE16S04 was shown to react with *D. bruxellensis* and weakly with *B. naardenensis*, BRE16S05 was shown to react with *D. anomala*, *D. bruxellensis*, and *B. naardenensis*. BRE26S12-14 and BRE26S16 were shown to react with only *D. bruxellensis*, whereas BRE26S17-21 were shown to react with both *D. anomala* and *D. bruxellensis*.

TABLE 4

|  | Dekkera Anomala | Dekkera Bruxellensis | Brettanomyces Custersianus | Brettanomyces naardenensis | Brettanomyces Nanus |
|---|---|---|---|---|---|
| Flu-BRE04 | − | + | − | +/− | − |
| Flu-BRE05 | + | + | − | + | − |
| Flu-BRE12 | − | + | − | − | − |
| Flu-BRE13 | − | + | − | − | − |
| Flu-BRE14 | − | + | − | − | − |
| Flu-BRE16 | − | + | − | − | − |
| Flu-BRE17 | + | + | − | − | − |
| Flu-BRE18 | + | + | − | − | − |
| Flu-BRE19 | + | + | − | − | − |
| Flu-BRE20 | + | + | − | − | − |
| Flu-BRE21 | + | + | − | − | − |

II. Dot blot of SBP-Labeled PNA Probes:

Using the procedures described above, total-RNA of each of the following yeast species potentially found in wine was prepared and then spotted on membranes: A *Dekkera bruxellensis*, NRRL #1411 B *Dekkera bruxellensis*, NRRL #1412 C *Dekkera bruxellensis*, NRRL #1413, D *Saccharomyces cerevisiae*, ATCC #4098 E *Saccharomyces kluyveri*, NRRL #Y-12651 F *Hanseniaspora occidentalis*, NRRL #Y-7946 G *Hanseniaspora valbyensis*, NRRL #Y-1626 H *Hanseniaspora guilliermondii*, NRRL #Y-1625 I *Hanseniaspora uvarum*, NRRL #Y-1614 J *Hanseniaspora osmophila*, NRRL #Y-1613 K *Hanseniaspora vineae*, NRRL #Y-17529 L *Candida stellata*, NRRL #Y-1446 M *Kloecker lindneri*, NRRL #Y-17531 N *Torulaspora delbrueckii*, NRRL #Y-866. Individual membranes were then placed in plastic bags and prehybridized in Hybridization Buffer 2 (25 mM Tris (pH 9.5), 1× Denhardt's solution, 50% (v/v) formamide, 0.7% (v/v) Tween 20, 1% Casein, 0.1 M NaCl, 5 mM EDTA) for 15 minutes at 50° C.

The SBP labeled PNA probes (BRE04, BRE05, BRE14 or BRE20) at 10 μM in Stabilization Buffer (See: Example 9) were then diluted 1:100 with Stabilization Buffer and finally mixed with a volume of Hybridization Buffer 2 so that final concentration of the probe was 1 nM.

The hybridization was performed at 50° C. for 30 minutes. The filters were then washed 3 times in Wash Solution (10 mM CAPSO (pH 10.0), 0.2% (v/v) Tween 20) at 50° C. for 10 minutes each.

Visualization of the Membrane:

After the washes were completed, the membranes were immersed in Substrate Solution (SuperSignal, Pierce) for 2 minutes. The membranes were placed in a plastic bag and excess substrate was squeezed out and the bag sealed. The membranes were exposed to Fuji-RX X-ray film for between 1 and 15 minutes.

With reference to FIG. 1, the specificity of the SBP-labeled PNA probes was examined. PNA probes BRE16S04, BRE16S05, BRE26S14, BRE26S20 were shown to react with only *D. bruxellensis*, and not substantially with any of the other yeast species tested. EuUNI1 (eucaryo-universal probe sequence (SBP-POO-ACC-AGA-CTT-GCC-CTC-EE-NH$_2$) was included as a positive control for the presence of yeast rRNA.

Figure 2A:
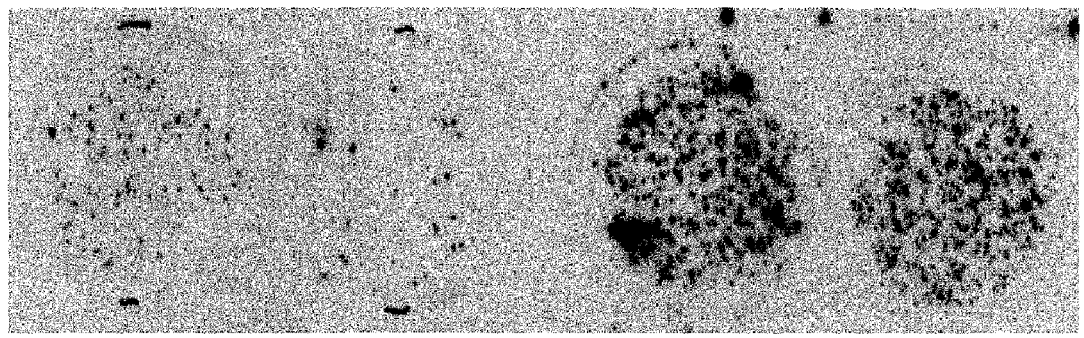
FIGS. 2A and 2B comprise panels that are electronic images of the X-ray film analysis of colonies (in duplicate) of yeast grown (directly on the round membrane filter) from filtered wine samples wherein the in-situ hybridization of the colonies with the SBP-labeled PNA probes is also performed directly on the membrane filter.
Figure 2B:
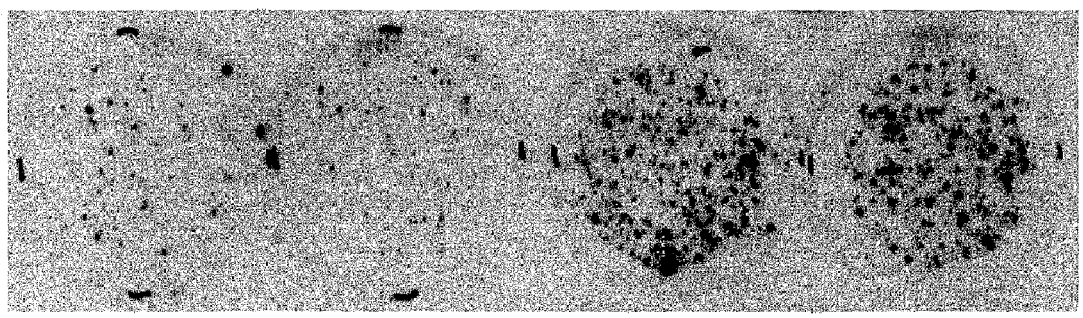
Figure 2C:
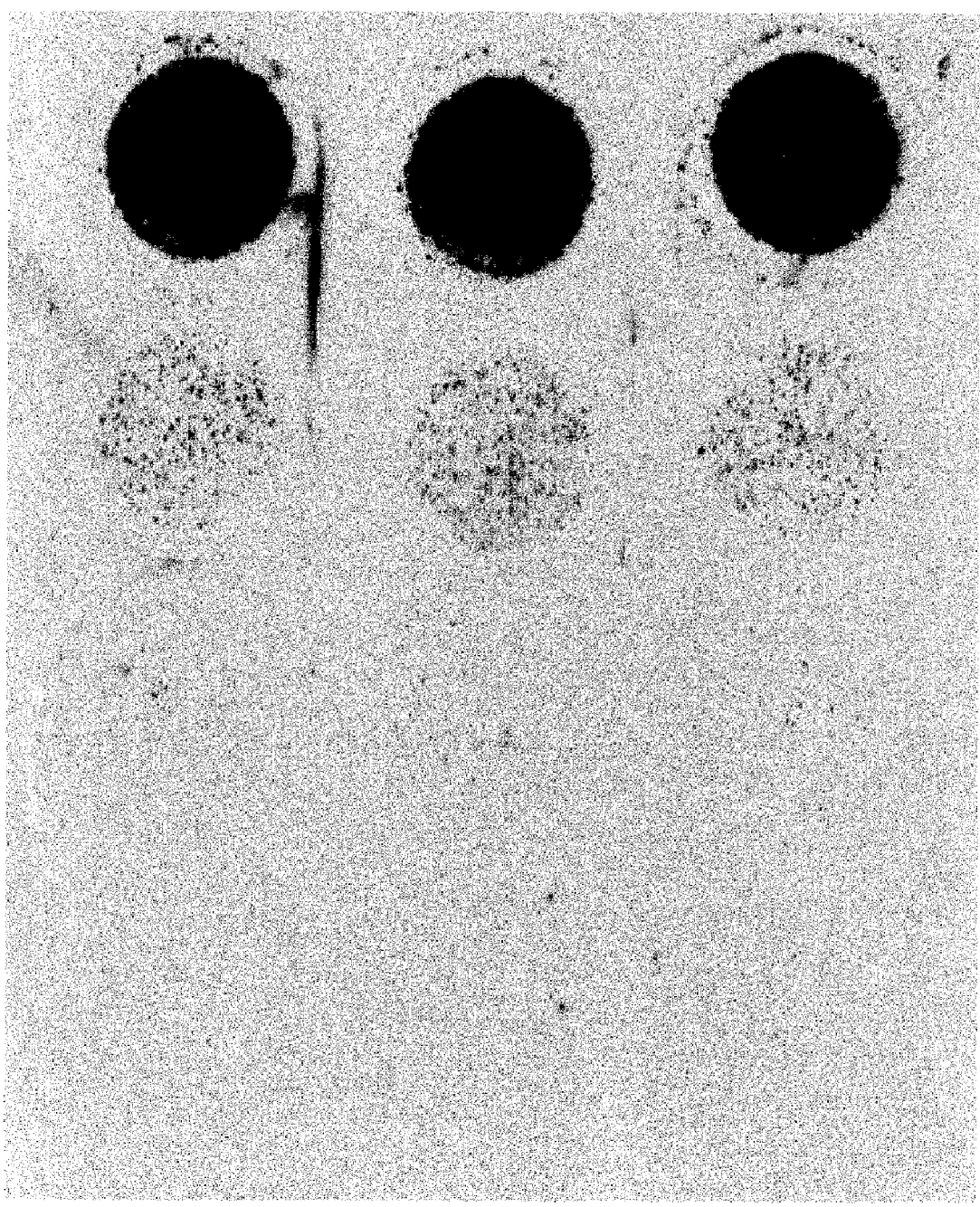
FIG. 2C comprises electronic images of the X-ray film analysis of colonies (in triplicate) of yeast grown (directly on the round membrane filter) from filtered wine samples wherein the in-situ hybridization of the colonies with the SBP-labeled PNA probes is also performed directly on the membrane filter.

III. Membrane-Based in-Situ Hybridization:

With reference to FIGS. 2A–C, the following wine samples were analyzed: #2, #28, and #30. These sample were all confirmed positive for *Brettanomyces*, the spoilage organism found in wine. Each sample was filtered through a 0.45 μm PVDF-membrane (P/N HVLP04700, Millipore Corp., MA) and rinsed with 10 mL of pre-filtered 2% Tween 80 followed by 25 mL of pre-filtered Milli-Q water. Volume filtered for each sample is indicated in the figures. The membrane was aseptically transferred to a petripad soaked with 2 mL of *Brettanomyces* Specific Media (BSM)-medium (Millipore) in a small petridish and incubated for minimum of 40 hours at 30° C. Prior to hybridization, microcolonies were fixed to the membrane by placing the membrane on another pad soaked with 1.5 mL of Fixation Solution (0.05% glutaraldehyde in ethanol) for 5 minutes. Hybridization was performed for 30 minutes at 50° C. in a petrislide (Millipore) with cover using 5 nM SBP-labeled PNA probe in Hybridization Buffer 2 (25 mM Tris (pH 9.5), 1× Denhardt's solution, 50% (v/v) formamide, 0.7% (v/v) Tween 20, 1% Casein, 0.1 M NaCl, 5 mM EDTA). Excess probe was removed by washing four times seven minutes in Wash Solution (10 mM CAPSO (pH 10.0), 0.2% (v/v) Tween 20). Hybridized probe was visualized by a 2 minute chemiluminescent reaction using 500 μL substrate (SuperSignal, Pierce) followed by a 15 minutes exposure on X-ray film (Fuji).

With reference to FIGS. 2A–C, the applicability of SBP-labeled PNA probes for simultaneous identification and enumeration of *Brettanomyces* (*Dekkera bruxellensis*) by membrane in situ hybridization within 1–3 days was examined. Each spot represents a microcolony (colony forming unit). *Brettanomyces* was detected in all samples and the number of spots follows the row of dilutions.

Example 11

Assay Combining Fixation and Hybridization in the Same Assay Step (i) Procedure

Both unadulterated and adulterated red wine samples spiked with *Brettanomyces*, the spoilage organism found in wine, were analyzed. Each sample of 1 mL volume was filtered through a 0.45 um PVDF filter membrane (Millipore Corp., MA) and rinsed with 10 mL of filter-sterilized 2% (v/v) Tween 80 followed by 25 mL of filter-sterilized Milli-Q water. The membrane was aseptically transferred to a petripad soaked with 2 mL of BSM medium (Millipore) in a small petridish and incubated for 1 day at 30° C. Fixation of the cells to the membrane in combination with hybridization of the probe to the targets were performed simultaneously for 30 minutes at 50° C. in a petrislide (Millipore)

with cover using 0.35% (v/v) glutaraldehyde and 5 nM SBP-labeled PNA probe (SBP-BRE14 or SBPZba03) in 1.5 mL of Hybridization Buffer (25 mM Tris (pH 9.5), 1× Denhardt's solution, 50% (v/v) formamide, 0.7% (v/v) Tween 20, 0.1% (w/v) casein, 0.1 M NaCl). Excess probe was removed by washing four times seven minutes in Wash Solution (10 mM CAPSO (pH 10.0), 0.2% (v/v) Tween 20). Hybridized probe was visualized by a 2 minute chemiluminescent reaction using 500 µL SuperSignal substrate (Pierce) followed by a 15 minutes exposure on X-ray film (Fuji).

TABLE 5

|  | Red wine | |
| --- | --- | --- |
|  | No *Brettanomyces* spike | *Brettanomyces* spike |
| SBP-BRE14 | − | + |
| SBP-Zba03 | − | − |

(ii) Result

The applicability of SBP-labeled PNA probes for simultaneous detection, identification, and enumeration of *Brettanomyces* (*Dekkera bruxellensis*) by membrane in situ hybridization in simultaneous combination with fixation was examined. With reference to Table 5, the results clearly demonstrate that the presence of the *Brettanomyces* that had been spiked into the red wine was detected using the procedure wherein fixation and hybridization are combined but that no *Brettanomyces* was detected in the unadulterated sample. Furthermore, no yeast were detected in either sample when a probe not specific to *Brettanomyces* was used. Therefore, the combination of fixation and hybridization as described does not appear to alter assay performance but the assay can be completed more rapidly in this format.

Example 12

Detection of Other Yeast Found in Wine:

(i) Procedure

Two samples of bottled White Zinfandel wine were analyzed. These samples were determined to be positive for *Zygosaccharomyces bailii*, a spoilage organism found in wine. Each sample of 1 mL volume was filtered through a 0.45 um PVDF filter membrane (Millipore) and rinsed with 10 mL of filter-sterilized 2% (v/v) Tween 80 followed by 25 mL of filter-sterilized Milli-Q water. The membrane was aseptically transferred to a petripad soaked with 2 mL of Yeast & Mold Media (YM) medium in a small petridish and incubated for 1 day at 30° C. Prior to hybridization, microcolonies were fixed to the membrane by placing the membrane on another pad soaked with 1.5 mL of Fixation Solution (0.035% (v/v) glutaraldehyde in denatured ethanol) for 5 minutes. Hybridization was performed for 30 minutes at 50° C. in a petrislide (Millipore) with cover using 5 nM SBP-labeled PNA probe (SBP-Zba03, SBPEuUni01 or ! SBPBRE14) in 1.5 mL of Hybridization Buffer (25 mM Tris (pH 9.5), 1× Denhardt's solution, 50% (v/v) formamide, 0.7% (v/v) Tween 20, 0.1% (w/v) casein, 0.1 M NaCl). Excess probe was removed by washing four times seven minutes in Wash Solution (10 mM CAPSO (pH 10.0), 0.2% (v/v) Tween 20). Hybridized probe was visualized by a 2 minute chemiluminescent reaction using 500 µL West Femto substrate (Pierce) followed by a 15 minutes exposure on X-ray film (Fuji).

TABLE 6

|  | Bottle #1 of White Zinfandel | Bottle #2 of White Zinfandel |
| --- | --- | --- |
| SBP-Zba03 | + | + |
| SBP-EuUni01 | + | + |
| SBP-BRE14 | − | − |
| No probe | − | − |

(ii) Result

The suitability of SBP-labeled PNA probes for simultaneous detection, identification, and enumeration of *Zygosaccharomyces bailii* by membrane in situ hybridization within 1–2 days was examined. With reference to Table 6, the results clearly demonstrate that *Zygosaccharomyces* bailii was detected using both the universal yeast probe (SBP-EuUni01) as well as the probe specific for *Zygosaccharomyces bailii* (SBP-Zba03). The control having no probe as well as the assay using the probe specific for *Brettanomyces* (SBP-Bre14) were blank. Thus, the results indicate that the procedure, when coupled with a probe of suitable nucleobase sequence, can be adapted for the specific detection of different the spoilage yeast *Zygosaccharomyces bailii*.

Example 13

Detection of Using Medical Important Yeast Using Universal Probes (i) Procedure

The following microorganisms or controls were analyzed: no sample, *Candida albicans* Y12983, *Candida dubliniensis* Y-17841, and *Candida glabrata*Y-65. Each sample of 1 mL volume was diluted in 0.15 M NaCl; filtered through a 37 nun Field Monitor (Millipore) containing a 0.45 um PVDF membrane (Millipore), both of which were sterilized by gamma-irradiation; and rinsed with 10 mL of filter-sterilized 2% (v/v) Tween 80 followed by 25 mL of filter-sterilized Milli-Q water. The membrane was aseptically transferred to a petripad soaked with 2 mL of YM medium in a small petridish and incubated for 17 hours at 30° C. Prior to hybridization, visible colonies were fixed to the membrane by placing the membrane on another pad soaked with 1.5 mL of Fixation Solution (0.35% (v/v) glutaraldehyde, 5 mM NaN$_3$, 0.01% (v/v) H$_2$O$_2$, 0.02% (w/v) acetophenetidin, 90% (v/v) denatured ethanol) for 5 minutes. Hybridization was performed for 30 minutes at 50° C. in a petrislide (Millipore) with cover using 5 nM SBP-labeled PNA probe (SBP-EuUni01 or SBP-BacUni01) in 1.5 mL of Hybridization Buffer (25 mM Tris (pH 9.5), 1× Denhardt's solution, 50% (v/v) formamide, 0.7% (v/v) Tween 20, 0.1% (w/v) casein, 0.1 M NaCl). Excess probe was removed by washing four times seven minutes in Wash Solution (10 mM CAPSO (pH 10.0), 0.2% (v/v) Tween 20). Hybridized probe was visualized by a 2 minute chemiluminescent reaction using 500 µL West Femto substrate (Pierce) followed by a 15 minutes exposure on X-ray film (Fuji).

TABLE 7

|  | No sample | *Candida albicans* | *Candida* | *Candida glabrata* |
| --- | --- | --- | --- | --- |
| SBP-EuUni01 | − | + | + | + |
| SBP-BacUni01 | − | − | − | − |

The applicability of SBP-labeled PNA probes for simultaneous identification and enumeration of *Candida albicans*, *Candida dubliniensis*, and *Candida glabrata* by membrane in situ hybridization within 24 hours was examined. With reference to Table 7, it is clear that the universal probe for detecting bacteria (SBP-BacUni01) was unreactive with the samples whereas the universal probe for detecting yeast species (SBP-EuUni01) produced a positive result in all but the negative (No Sample) control. Consequently, the data indicates that the procedure and probes can be used to detect yeast of medicinal significance.

Example 14

Detection of *Brettanomyces* by PNA-FISH (i) Materials and Methods:

Yeast strains: Five type strains representing the five *Dekkera* and *Brettanomyces* species, ten reference strains representing synonyms of Dekkera bruxellensis, twenty six yeast species potentially found in wine, seventy eight wine isolates of *Brettanomyces*, and eight wine isolates of cycloheximide-resistant spheroidal yeast were collected from various sources (see Table 2–6). The spheroid yeast were included because they grow relatively slowly on cycloheximide containing media—like *Brettanomyces*- and may therefore be misidentified as *Brettanomyces*. Strains were grown to visible colonies on YM agar at 30° C.

Preparation of smears: For each smear, one drop of PBS was placed in the well of a Teflon-coated microscope slide (Erie Scientific, Portsmouth, N.H.). A small portion of a colony was picked using a clean, sterile toothpick and suspended in the PBS by gently mixing in the microscope well. The slide was then placed on a 50° C. slide warmer for 30 min at which point the smears were dry.

Fluorescence in situ hybridization (FISH): Smears were covered with approximately 20 L of hybridization solution containing 10% (w/v) dextran sulfate (Sigma Chemical Co., St. Louis, Mo.), 10 mM NaCl (J. T. Baker), 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM Na$_2$EDTA (Sigma), 0.1% (v/v) Triton X-100 (Aldrich), 50 mM Tris/HCl pH 7.5 and 100 nM fluorescein-labeled PNA probe (Flu-BRE14). Coverslips were put on the smears to ensure even coverage with hybridization solution, and the slides were subsequently placed on a slide warmer with a humidity chamber (Slidemoat, Boeckel, Germany) and incubated for 30 min at 50° C. Following hybridization, the coverslips were removed by submerging the slides into pre-warmed 25 mM Tris, pH 7.6, 137 mM NaCl (J. T. Baker), 3 mM KCl (Sigma) in a water bath at 50° C. and washed for 30 min. The slides were then cooled to room temperature by brief immersion in H$_2$O and dried following a brief immersion in ethanol. Each smear was finally mounted using one drop of IMAGEN Mounting Fluid (DAKO, Ely, UK) and covered with a coverslip. Microscopic examination was conducted using a fluorescence microscope (Optiphot, Nikon Corporation, Tokyo, Japan) equipped with a 60×/1.4 oil objective (Nikon), an HBO 100 W mercury lamp, and a FITC/Texas Red dual band filter set (Chroma Technology Corp., Brattleboro, Vt.).

(ii) Results

Initially, the specificity of the PNA probe labeled with fluorescein (Flu-BRE14) was tested by FISH using type strains of the five species of *Dekkera* and *Brettanomyces* (Table 8) as well as ten reference strains representing different synonyms of Dekkera bruxellensis (Table 9).

Twenty-six other yeast species potentially found in wine were also examined for reactivity with the probe (Table 10). As predicted from the alignment of sequences in the target area, Flu-BRE14 hybridized only to the type strain *D. bruxellensis* and synonyms thereof, whereas it did not detect any of the other 26 yeast species. When taken as a whole, there results demonstrate that the PNA-FISH using Flu-BRE14 can be used to specifically detect *Brettanomyces*, the spoilage organism in wine.

TABLE 8

Detection of *Dekkera* and *Brettanomyces* type strains of accepted species with Flu-BRE14

| Organism | Strain no. | Result |
| --- | --- | --- |
| Dekkera anomala | NRRL Y-17522 | Neg. |
| Dekkera bruxellensis | NRRL Y-12961 | Pos. |
| Brettanomyces naardenensis | NRRL Y-17526 | Neg. |
| Brettanomyces custersianus | NRRL Y-6653 | Neg. |
| Brettanomyces nanus | NRRL Y-17527 | Neg. |

NRRL: Agricultural Research Service (ARS) Culture Collection, Peoria, IL.

TABLE 9

Detection of *Dekkera bruxellensis* reference strains (synonyms) with Flu-BRE14.

| Organism | Strain no. | Result |
| --- | --- | --- |
| Brettanomyces bruxellensis | NRRL Y-1411 | Pos. |
| Brettanomyces lambicus | NRRL Y-1413 | Pos. |
| Mycotorula intermedia | NRRL Y-17534 | Pos. |
| Brettanomyces bruxellensis | NRRL Y-1412 | Pos. |
| Brettanomyces schanderlii | NRRL Y-17523 | Pos. |
| Brettanomyces abstinens | NRRL Y-17525 | Pos. |
| Dekkera intermedia | ATCC 52904[1] | Pos. |
| Dekkera intermedia | ATCC 56869 | Pos. |
| Dekkera intermedia | ATCC 64276 | Pos. |
| Dekkera lambica | ATCC 10563[2] | Pos. |

[1] = NRRL Y-17523.
[2] = NRRL Y-1413
NRRL: Agricultural Research Service (ARS) Culture Collection, Peoria, IL.
ATCC: American Type Culture Collection, Manassas, VA.

TABLE 10

Reaction of other yeast species potentially found in wine with Flu-BRE14.

| Organism | Strain no. | Result |
| --- | --- | --- |
| Hanseniaspora warum | NRRL Y-1614 | Neg. |
| Hanseniaspora guilliermondii | NRRL Y-1625 | Neg. |
| Hanseniaspora occidentalis | NRRL Y-7946 | Neg. |
| Hanseniaspora osmophila | NRRL Y-1613 | Neg. |
| Hanseniaspora valbyensis | NRRL Y-1626 | Neg. |
| Hanseniaspora vineae | NRRL Y-17529 | Neg. |
| Kloeckera lindneri | NRRL Y-17531 | Neg. |
| Torulaspora delbrueckii | NRRL Y-866 | Neg. |
| Debaryomyces hansenii | NRRL Y-7426 | Neg. |
| Debarymyces carsonii | NRRL YB-4275 | Neg. |
| Candida stellata | NRRL Y-1446 | Neg. |
| Metschnikowia pulcherrima | NRRL Y-7111 | Neg. |
| Rhodotorula fujisanensis | NRRL YB-4824 | Neg. |
| Rhodotorula glutinis | NRRL Y-2502 | Neg. |
| Rhodotorula graminis | NRRL Y-2474 | Neg. |
| Schizosaccharomyces pombe | NRRL Y-12796 | Neg. |
| Pichia anomala | NRRL Y-366 | Neg. |
| Pichia membranifaciens | NRRL Y-2026 | Neg. |
| Pichia farinosa | NRRL Y-7553 | Neg. |
| Saccharomyces cerevisiae | ATCC 4098 | Neg. |
| Saccharomyces kluyveri | NRRL Y-12651 | Neg. |
| Saccharomycodes ludwigii | NRRL Y-12793 | Neg. |
| Zygosaccharomyces bailii | ATCC 66825 | Neg. |

TABLE 10-continued

Reaction of other yeast species potentially found in wine with Flu-BRE14.

| Organism | Strain no. | Result |
|---|---|---|
| Zygosaccharomyces bisporus | NRRL Y-12626 | Neg. |
| Zygosaccharomyces rouxii | NRRL Y-229 | Neg. |
| Zygosaccharomyces florentinus | NRRL Y-1560 | Neg. |

NRRL: Agricultural Research Service (ARS) Culture Collection, Peoria, IL.
ATCC: American Type Culture Collection, Manassas, VA.

Equivalents

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A method comprising:
   a) contacting one or more species of yeast in a sample with one or more yeast specific enzyme-linked probes, under suitable in-situ hybridization conditions, to thereby form one or more probe/target sequence hybrids within the yeast; and
   b) detecting enzyme activity of the enzyme-linked probe or probes within the yeast to thereby determine the presence, absence, identity or number of yeast in the sample.

2. The method of claim 1 further comprising:
   c) isolating the yeast using a filter as an isolation medium.

3. The method of claim 2, further comprising:
   d) growing the isolated yeast by culture in media.

4. The method of claim 3, wherein the culture is grown directly on the filter, under suitable culture conditions, by placing the filter in contact with media.

5. A method for detecting, identifying or quantitating Dekkera/Brettanomyces yeast in a sample; said method comprising:
   a) contacting one or more species of yeast in the sample with one or more Dekkera/Brettanomyces yeast specific probes, under suitable hybridization conditions, to thereby form a probe/target sequence hybrid; and
   b) detecting the presence, absence or amount of probe/target sequence hybrid and correlating the result with the presence, absence or number of Dekkera/Brettanomyces yeast in the sample;
   wherein one or more of the Dekkera/Brettanomyces yeast specific probes comprise a probing nucleobase sequence wherein at least a portion of the probing nucleobase sequence is at least ninety percent homologous to the nucleobase sequences selected from the group consisting of: AGC-GGG-TCT-ATT-AGA (Seq. ID No. 1); CCA-GGT-GAG-GTC-CGC (Seq. ID No. 2); CGG-TTG-CCC-GAT-TTC (Seq. ID No. 3); TCG-CCT-TCC-TCC-TCT (Seq. ID No. 4); CGG-TCT-CCA-GCG-ATT (Seq. ID No. 5); CAC-AAG-ATG-TCC-GCG (Seq. ID No. 6); GCG-GGC-ACT-AAT-TGA (Seq. ID No. 7); CAT-CCA-CGA-GGA-ACG (Seq. ID No. 8); GTG-TAA-ACC-AGG-TGC (Seq. ID No. 9); ATG-GCT-CCC-AGA-ACC (Seq. ID No. 10) and GAC-AGA-ATC-GAA-GGG (Seq. ID No. 11) and sequences fully complementary thereto and of the same length.

6. The method of claim 5, wherein the probing nucleobase sequences of said one or more probes are selected to be one hundred percent homologous to a nucleobase sequence identified in the claim.

7. A method comprising:
   a) filtering a fixed volume of a liquid sample comprising yeast using a filter having a pore size that does not allow the yeast to pass;
   b) incubating the filter containing the yeast, in media and under culture conditions, for 45 or fewer hours to thereby grow microcolonies of the yeast;
   c) fixing the microcolonies of the yeast to the filter;
   d) contacting the microcolonies of the yeast with a yeast specific enzyme-linked probe, under suitable in-situ hybridization conditions, to thereby form one or more probe/target sequence hybrids within the yeast;

e) detecting enzyme activity probe or probes within the yeast to thereby determine the presence, absence or number of yeast sought to be detected in the sample; and f) determining the quantity of the yeast in the sample;

wherein the yeast are slow growing and the method is performed within 48 hours.

8. The method of claim 7, wherein fixing the microcolonies of yeast to the filter and contacting the microcolonies of yeast with a yeast specific enzyme-linked probe are performed simultaneously using a single solution.

9. The method of claim 7, wherein the number of CFU in the sample is determined.

10. The method of claim 4, wherein colonies grown on the filter represent the number of colony forming units (CFU) present in the sample.

11. The method of claim 3, wherein the yeast are slow growing yeast.

12. The method of claim 11, wherein the identity and number of slow growing yeast in the culture is determined within 48 hours.

13. The method of claim 1, wherein the target sequence is ribosomal RNA.

14. The method of claim 13, wherein the ribosomal RNA target sequence is specific for detecting *Dekkera/Brettanomyces* yeast in the sample.

15. The method of claim 13, wherein the ribosomal RNA target sequence is specific for detecting *Dekkera bruxellensis* yeast in the sample.

16. The method of claim 1, wherein the one or more yeast specific enzyme-linked probes are selected to detect a particular species of yeast.

17. The method of claim 1, wherein the one or more yeast specific enzyme-inked probes are selected to detect members of a genus of a yeast.

18. The method of claim 1, wherein the one or more yeast specific enzyme-linked probes are selected to detect all yeast present in the sample.

19. The method of claim 1, wherein the enzyme-linked probe is an enzyme-linked peptide nucleic acid probe.

20. The method of claim 19, wherein the probe is a soy bean peroxidase labeled peptide nucleic acid probe.

* * * * *